United States Patent
Hess et al.

(10) Patent No.: US 9,604,242 B2
(45) Date of Patent: Mar. 28, 2017

(54) VOLATILE LIQUID DROPLET DISPENSER DEVICE

(75) Inventors: Joseph Hess, Bevaix (CH); Amir Feriani, Auvernier (CH); Luciano Cravero, Cressier (CH); Stewart Noble, Perpetua de Mogoda (ES); Victor Ques, Perpetua de Mogoda (ES)

(73) Assignee: APTAR FRANCE SAS, Le Neubourg (FR)

( * ) Notice: Subject to any disclaimer, the term of this patent is extended or adjusted under 35 U.S.C. 154(b) by 2141 days.

(21) Appl. No.: 12/095,695

(22) PCT Filed: Jun. 23, 2006

(86) PCT No.: PCT/EP2006/006059
§ 371 (c)(1),
(2), (4) Date: Nov. 4, 2010

(87) PCT Pub. No.: WO2007/062698
PCT Pub. Date: Jun. 7, 2007

(65) Prior Publication Data
US 2011/0036921 A1    Feb. 17, 2011

(30) Foreign Application Priority Data
Nov. 30, 2005 (EP) ................... 05026083

(51) Int. Cl.
*A24F 25/00*  (2006.01)
*B05B 17/00*  (2006.01)
(Continued)

(52) U.S. Cl.
CPC ............ *B05B 17/0638* (2013.01); *A61L 9/01* (2013.01); *A61L 9/127* (2013.01); *A61L 9/145* (2013.01);
(Continued)

(58) Field of Classification Search
CPC ............ B05B 17/0676; B05B 17/0684; B05B 17/0638; B05B 17/0669; B05B 17/0646; A61L 9/01; A61L 9/145; A61L 9/127
(Continued)

(56) References Cited

U.S. PATENT DOCUMENTS 3,900,162 A * 8/1975 Titus ................... B41J 2/025
                                                  239/102.2
4,667,877 A    5/1987 Yao et al.
(Continued)

FOREIGN PATENT DOCUMENTS

EP    0 516 565 A1    2/1992
EP    0 641 934 A1    3/1995
(Continued)

OTHER PUBLICATIONS

E-Mail from Elson Silva, "Respecting Hydrology Science—US Pat. Application 20110036921", ECOLAB, Inc., dated Feb. 17, 2011, pp. 1-6.
(Continued)

*Primary Examiner* — Len Tran
*Assistant Examiner* — Joel Zhou
(74) *Attorney, Agent, or Firm* — Griffin and Szipl PC

(57) ABSTRACT

A volatile liquid droplet dispenser for containing a liquid to be dispensed, with a first substrate having a space for containing the liquid, and having an outlet with at least one outlet nozzle, the first substrate further having the space adjacent to the liquid outlet, to receive the liquid such that the liquid may exit through at least one outlet nozzle of the outlet, a second substrate having a liquid inlet, and an actuating membrane arranged to actuate liquid in the space. The first substrate also has a fluidic channel interconnected to the space and arranged to laterally connect the liquid inlet to the space, thereby conveying the liquid to the space by
(Continued)

way of lateral capillary action. The outlet is eccentric to the liquid inlet and in a vertical plane that is substantially the same or lower than the plane of the liquid inlet, depending on the liquid used.

18 Claims, 20 Drawing Sheets

(51) Int. Cl.
*A61L 9/01* (2006.01)
*A61L 9/12* (2006.01)
*A61L 9/14* (2006.01)
*B05B 17/06* (2006.01)

(52) U.S. Cl.
CPC ...... *B05B 17/0669* (2013.01); *B05B 17/0676* (2013.01); *B05B 17/0684* (2013.01); *B05B 17/0646* (2013.01)

(58) Field of Classification Search
USPC ..................................... 239/44, 102.1, 102.2
See application file for complete search history.

(56) References Cited

U.S. PATENT DOCUMENTS

| | | | |
|---|---|---|---|
| 4,667,977 A | 5/1987 | Lacroix | |
| 4,702,418 A | 10/1987 | Carter et al. | |
| 4,923,448 A | 5/1990 | Ennis, III | |
| 5,462,839 A | 10/1995 | de Rooij et al. | |
| 5,662,835 A | 9/1997 | Collingwood | |
| 5,749,519 A | 5/1998 | Miller | |
| 5,792,941 A | 8/1998 | Rye et al. | |
| 6,062,212 A | 5/2000 | Davison et al. | |
| 6,116,517 A * | 9/2000 | Heinzl ................. | B41J 2/14282 239/101 |
| 6,341,732 B1 * | 1/2002 | Martin ................ | B05B 17/0684 128/200.16 |
| 6,378,780 B1 | 4/2002 | Martens, III et al. | |
| 6,439,474 B2 * | 8/2002 | Denen .................. | A01M 1/205 239/102.1 |
| 6,443,366 B1 | 9/2002 | Hirota et al. | |
| 6,536,682 B1 | 3/2003 | Schnupp et al. | |
| 6,554,201 B2 | 4/2003 | Klimowicz et al. | |
| 6,722,582 B2 | 4/2004 | Hess et al. | |
| 6,732,944 B2 | 5/2004 | Litherland et al. | |
| 6,766,817 B2 | 7/2004 | da Silva | |
| 6,802,460 B2 | 10/2004 | Hess et al. | |
| 6,918,404 B2 | 7/2005 | Dias da Silva | |
| 6,926,208 B2 | 8/2005 | Ivri | |
| 7,066,398 B2 | 6/2006 | Borland et al. | |
| 7,066,586 B2 | 6/2006 | da Silva | |
| 7,244,398 B2 | 7/2007 | Kotary et al. | |
| 7,285,255 B2 | 10/2007 | Kadlec et al. | |
| 2002/0162551 A1 | 11/2002 | Litherland | |
| 2002/0162898 A1 | 11/2002 | Klimowicz et al. | |
| 2002/0175220 A1 * | 11/2002 | Pence ................. | B05B 17/0646 239/102.2 |
| 2004/0082076 A1 * | 4/2004 | Zengerle .............. | B01J 19/0046 436/180 |
| 2004/0263567 A1 * | 12/2004 | Hess ................... | B05B 17/0638 347/47 |
| 2005/0001050 A1 * | 1/2005 | Takagi ................. | B01L 3/0268 239/4 |
| 2005/0201870 A1 * | 9/2005 | Koerner .............. | B05B 17/0646 417/322 |
| 2005/0207917 A1 * | 9/2005 | Koerner ............ | A61M 15/0065 417/413.2 |
| 2008/0015531 A1 | 1/2008 | Hird et al. | |

FOREIGN PATENT DOCUMENTS

| | | |
|---|---|---|
| EP | 0 897 755 A | 2/1999 |
| EP | 0 923 957 A1 | 6/1999 |
| EP | 0923957 A1 | 6/1999 |
| EP | 1 092 541 A2 | 4/2001 |
| EP | 1129741 A2 | 9/2001 |
| EP | 1 150 779 | 11/2001 |
| EP | 1 236 517 A1 | 9/2002 |
| EP | 1273355 A1 | 1/2003 |
| EP | 1 430 958 A2 | 6/2004 |
| EP | 1602414 A2 | 12/2005 |
| EP | 1604701 A1 | 12/2005 |
| EP | 1 952 896 A1 | 8/2008 |
| JP | 2000-051755 A | 2/2000 |
| WO | 95/15822 A1 | 6/1995 |
| WO | 00/47335 | 8/2000 |
| WO | 01/97982 A1 | 12/2001 |
| WO | 03/009871 A2 | 2/2003 |
| WO | 03068413 A1 | 8/2003 |
| WO | 03/082477 A1 | 10/2003 |
| WO | 2004031580 A1 | 4/2004 |
| WO | 2004/043502 A1 | 5/2004 |
| WO | 2005024967 A1 | 3/2005 |
| WO | 2005097349 A1 | 10/2005 |
| WO | 2007062698 A1 | 6/2007 |

OTHER PUBLICATIONS

Non-Final Office Action issued in co-pending U.S. Appl. No. 12/477,646, dated Mar. 8, 2011.
E-mail from Elson da Silva discussing "Know-How and IP in Applied Hydrology," sent Sep. 11, 2008.
European Search Report, completed Apr. 3, 2007, Application No. 07002190.
International Search Report, issued in corresponding application No. EP 08157455.0 completed Oct. 7, 2008, mailed Oct. 14, 2008.
Random House Webster's College Dictionary 845 (1991).
McGraw-Hill Dictionary of Scientific and Technical Terms 663 (1978).
Hans C. Ohanian, Physics, 390-395 (1985).
Hans C. Ohanian, Physics 356-359 (W.W. Norton & Co., Inc. 1985), filed in co-pending related U.S. Appl. No. 12/024,310 as Exhibit A2.
Random House Webster's College Dictionary 87, 903 and 1295 (1991), filed in co-pending related U.S. Appl. No. 12/024,310 as Exhibit B2.
Stephen F. Pond, Inkjet Technology and Product Development Strategies 105-108 (Torrey Pines Research 2000), filed in co-pending related U.S. Appl. No. 12/024,310 as Exhibit C2.
"Vibration Induced Drop Atomization (VIDA)" at http://www.me.gatech.edu/bvukasinovic/VIDA.html, downloaded Aug. 1, 2011 (one page), filed in co-pending related U.S. Appl. No. 12/024,310 as Exhibit D2.
"VIDA Dynamics" at http://me.gatech.edu/bvukasinovic/VIDAdynamics.html, downloaded Aug. 1, 2011 (2 pages), filed in co-pending related U.S. Appl. No. 12/024,310 as Exhibit E2.
Office Action issued in corresponding U.S. Appl. No. 12/024,310, dated Jun. 28, 2010.
International Search Report issued in corresponding European Application No. PCT/EP2006/006059, completed Aug. 7, 2006, mailed Aug. 14, 2006.
Final Office Action issued in co-pending U.S. Appl. No. 12/477,646 on Feb. 22, 2013.
Definition of "between", Random House Webster's College Dictionary 130 (1991), filed in co-pending related U.S. Appl. No. 12/477,646 with Amendment (E).
Hans C. Ohanian, Physics, 452-461, W.W. Norton & Co. 1985.
Office Action issued in co-pending related U.S. Appl. No. 12/024,310 on Mar. 14, 2014.

* cited by examiner

VOLATILE LIQUID DROPLET DISPENSER DEVICE

This is a National Phase Application in the United States of International Patent Application No. PCT/EP/2006/006059 filed Jun. 23, 2006, which claims priority on European Patent Application No. 05026083.5, filed Nov. 30, 2005. The entire disclosures of the above patent applications are hereby incorporated by reference.

FIELD OF THE INVENTION

The present invention relates to a volatile liquid droplet dispenser device for connection with a disposable external reservoir containing a volatile liquid substance to be dispensed as a liquid droplet spray from the volatile liquid device, in which the liquid may be for example an ambient fragrance, a perfume, an insecticide and aqueous based liquids. Volatility can be implied through the nature of the solvent, but also through the extremely small size of droplets leading to quick evaporation or a combination of the two characteristics. Such a device may be used for controlled release of droplets of such volatile liquids.

BACKGROUND OF THE INVENTION

Various devices are known for dispensing a volatile liquid. For example, an air freshening dispenser device is known from the document U.S. Pat. No. 5,749,519. This device relates to an air freshener that has a reservoir for containing an air freshener liquid. The reservoir is connected to a vapour-emanating surface of a liquid dispensing device by way of a wick. The vapour emanating surface is initially covered with a peal-off seal means. Once the seal means pealed off, the liquid is transmitted from the reservoir via the wick through capillary action directly to the vapour-emanating surface so as to dispense the air freshener.

Due to its design, and in particular due to the use of capillary action and wicking pressure, the liquid dispensing device always transmits the liquid to the vapour-emanating surface means. Thus, to avoid the ensuing waste and spill, the device is provided in a housing having a cover for sealing the vapour-emanating surface means. Once the cover is removed, the vapour is continuously dispensed into the surrounding air. Hence controlled release of the evaporation is not possible.

This leads to excessive dispensing of liquid if one does not want to fragrance a room for example, but forgets to put the cover back on, and it becomes impossible to allow for a controlled dispersion of the vapour amount. It further leads to the phenomenon of olfactory fatigue, a condition where one does not perceive the refreshing odour any longer because of habituation.

Another device is known from the document U.S. Pat. No. 5,662,835 in which a liquid chemical agent is transported from a supply to an emanating surface from which an airflow provided by a ventilator facilitates the diffusion of the liquid chemical agent into the air. The document discloses means for interrupting the transportation of the chemical agent from the supply to the emanating surface. The means for interrupting the transport of the chemical agent are described as being provided initially and then being broken as soon as the device is put into service, much like disclosed by the previous document. From then on the device always emits the chemical agent at some significant level, unless an additional closure is provided. The level can be further modulated by the use of a fan, but can in principle only be increased above a base level.

Another device is known from the document U.S. Pat. No. 6,341,732 in which the liquid to be expelled is supplied from a wick straight up to the underside of a superposed vibrating dome-shaped orifice plate where the liquid flows through capillary action through orifices in the plate and is then ejected in a timed fashion from its upper side through the action of the vibrating orifice plate. Liquid which passes through the orifices in the dome region of the plate, but which has not been ejected, is directed back down through larger openings in a lower region of the plate. The liquid also flows back onto the wick, which places it in continuous capillary communication along the underside of the plate with the atomizing orifices. In this context, corresponding document WO01/97982 relating to the same device is more explicit regarding that sort of functionality.

Thus this device actually has a 2-phase mode of continuous function:
a) continuous evaporation as described above, and
b) additional timed ejection via the vibrating orifice plate The continuous evaporation alone can be found to be in the range of 100 mg/day without any piezo actuated time emission. Consequently the device has the problem of in fact never being off, but diffusing at a continuous rate and dispensing in a timed fashion at a higher rate. This, as with the previously cited device, leads to the phenomenon of olfactory fatigue, where the user doesn't notice the odour anymore over time and where the fragrance including the solvents are actually continuously and uselessly dispensed in the air. Also, this device requires a complicated construction to hold the plate vibration actuation means at a particular distance from the wick. The device has a further problem in that because of the continuously wet outside surface of the orifice plate, some larger droplets might be expelled, which can cause the liquid to fall-out, meaning not being ejected in the air to evaporate but falling back on the surface where the device is placed. Additional problems result from the fact that the outside surface of the orifice plate actually accommodates the piezoelectric vibrating element and the connectors and that the continued liquid and solvent supply over these surfaces requires particular attention in order to provide long-term reliability. Avoiding this problem leads to complicated surface treatment and electronics and to a certain limitation of liquids that can be expelled without this phenomenon of fall-out and other functional decay. This device further has a problem of causing a wetting of fingers or hands of a user when changing the disposable reservoir. Further, it is very difficult to control the amount of liquid ejected, which is why peripheral orifices are provided to recuperate liquid that has not been ejected.

Additional features of the same known device are disclosed in document U.S. Pat. No. 6,439,474, introducing a battery driven piezoelectric atomizer that is controlled by decreasing vibration amplitude and by executing a frequency sweep during the decreasing amplitude.

In this device the liquid is supplied by a wick from a reservoir directly to the domed region in the underside of a circular membrane that is vibrated by an annular piezoelectric actuator in known fashion. The vibration is controlled by a driving sequence, where driving and sleeping periods of differing lengths alternate. The battery supply voltage of 1.5 Volt is first increased via a charge pump to 3.3 Volt, related to the highest vibration amplitude. The drive period starts initially at the highest voltage supplied by the charge pump, which then decreases as determined by an RC timing circuit.

Hence the voltage decrease happens exponentially as given by that sort of circuit and determines the duration of the fixed drive period. Its lowest level is chosen to still ensure proper functioning of the device. During part of the sleep period, the battery is recharged to allow for a further drive period. Different intensities are programmable by varying the duration of the sleep period. As said before, during the sleep period the device continues to evaporate the liquid passively in the particular passive evaporation mode of the 2-phase mode of continuous device function. The device further uses a frequency sweep mode to accommodate for inter-device device variations.

Another droplet spray device is known from the document U.S. Pat. No. 6,062,212 which describes a liquid dispenser having vibration means which are activated to expel a metered dose of liquid deposited on a mesh from that mesh in the usual manner. The vibration means remain activated longer than necessary to expel the metered dose of liquid to ensure a complete emptying of the liquid from the dispenser. The disadvantage is that this additional atomising duration will sometimes be either too long or too short and that a fixed time will not work with liquids of varying viscosities, surface tensions and ambient conditions, as is the case with liquids containing volatile solvents.

Another atomising device is known from the document WO 03/082477 A1, disclosing the surface treatment of the outer side of a vibrating orifice atomizer in such a manner as to resist wetting and liquid build-up.

Another device is known from the document U.S. Pat. No. 4,702,418 which describes a piezoelectric aerosol dispenser that has eccentric liquid inlet/outlet means, and a nozzle chamber having a nozzle region proximate a single nozzle and a larger reservoir interconnected to the nozzle region. The nozzle region is gravity fed through a restrictive channel. Further, a piezoelectric bender is used to drive fluid from the reservoir region to the nozzle region and from the nozzle region through the single nozzle to create an aerosol spray. Such an arrangement with a piezoelectric bender does not allow for a controlled release of fluid, as the fluid must first be pumped from the reservoir region and then expelled from the nozzles without interference of one flow with the other. Further, precise control while using a piezoelectric bender is virtually impossible.

Another device is known from the document EP 1 150 779 which describes a piezoelectric spraying system for dispensing volatiles. The atomisation method relates to a device that uses a wick to transfer a liquid to a vibrating orifice plate, the liquid having certain characteristics known from fragrance formulations.

Yet another device is known from EP 1 430 958 which discloses a liquid supply package comprising a liquid container with a wick extending just above the top of the container and supplying liquid having basically the same characteristics as noted in the previous document.

It should be noted that in both these cases as well as other prior art wick-fed atomizers using a vibrating orifice plate as outlet means with generally tapered shaped orifices, the vertical and centric liquid feeding arrangement always needs to put the liquid feeding point underneath the outlet means. This has two drawbacks. The shape of the orifices facilitates oozing, increased passive evaporation and the position of the wick with regards to the outlet means limits the height and volume of the container via a particular wick length at which reliable continuous feed can still be achieved, specially over a certain range of viscosity and density. In fact applicant has observed that as of a particular height of reservoir or length of wick, the liquid does no longer get to a feeding point underneath the outlet means, but flows back into the reservoir and hence "starves" the atomizer. Consequently, the resulting devices are known to have very small and low profile liquid containers, limiting the useful life of a refill and also need particularly volatile ingredients with potentially ensuing VOC problems.

Document WO 2005/097349 discloses a very similar device using a compressible wick with a compliant upper wick section in direct contact with the vibrating orifice plate.

Other devices are disclosed which deliver several volatile liquids and coordinate delivery with light, sound, motion, temperature and the like such as WO 03/09871 and WO 04043502, where however the continuous evaporation persists and hence also the problems of olfactory fatigue and unsatisfactory delivery control. These devices therefore appear at odds with the objective of creating a precise ambiance at a particular time depending on and in coordination with sound, light and the like. Indeed the efficiency of olfactory sensorial performance hinges on the effect that "now the scent is not present"; and "suddenly, i.e. shortly after a particular musical theme or shortly after turning on the lights" and the like, it is present.

It is, therefore, an object of the present invention to provide a volatile liquid dispenser device that overcomes the abovementioned inconveniences of olfactory fatigue, of continuous evaporation of fragrances and solvents, of insufficient delivery control, of reservoir limitations and of fall-out.

It is a further objective of the present invention to provide controlled release of liquid substances such as fragrances, aromas, hydrolates, essential oil formulations, non-aqueous solvent based liquids and certain aqueous liquids including those containing surfactants, medication agents and the like, dispensed in very small droplets by such a device.

It is another object of the present invention to provide such a device that is simple in construction, reliable and inexpensive to manufacture, small in size, flexible with regards to liquid properties and reservoir volume as well as low in energy consumption and cost.

SUMMARY OF THE INVENTION

Thus, the present invention concerns a volatile liquid droplet dispenser device. In accordance with a first non-limiting illustrative embodiment of the present invention, a volatile liquid droplet dispenser device is provided for containing a liquid substance to be dispensed, wherein the device includes: (a) a first substrate (11, 111, 112) having a space (13, 131, 132) for containing the liquid substance, and having liquid outlet means (14, 141, 142), wherein the liquid outlet means (14, 141, 142) comprise at least one outlet nozzle (14c) for ejecting liquid substance there through, and the first substrate (11, 111, 112) further has the space (13, 131, 132) arranged proximate to the liquid outlet means (14, 141, 142) and to receive the liquid substance such that the liquid substance may exit the space (13, 131, 132) of the device by traversing the at least one nozzle (14c) of the liquid outlet means (14, 141, 142); (b) a second substrate (21, 211, 212) having a liquid inlet means (41, 411, 412) for allowing the liquid substance to enter the device; and (c) an actuating membrane (31, 311, 312), arranged to actuate liquid substance in the space (13, 131, 132) such that the liquid substance undergoes a vibration and contacts the liquid outlet means (14, 141, 142) thereby exiting the device as a liquid droplet spray, wherein the first substrate (11, 111, 112) further comprises a fluidic channel (13c, 131c, 132c) interconnected to the space (13, 131, 132) and arranged to laterally connect the liquid inlet means (41, 411, 412) to the space thereby conveying the liquid substance to the space (13, 131, 132) by way of lateral capillary action, and the liquid outlet means (14, 141, 142) is arranged eccentric to the liquid inlet means (41, 411, 412) and in a vertical plane that is substantially the same or lower than the plane of the liquid inlet means depending on the liquid substance properties dimensions.

In accordance with a second illustrative, non-limiting embodiment of the present invention, the first non-limiting embodiment is modified so that it further comprises a reservoir (R, 13R) for containing the liquid substance. In accordance with a third illustrative, non-limiting embodiment, the second non-limiting embodiment is further modified so that the reservoir is an external reservoir (R), and wherein the first substrate (112) or the second substrate (21, 211) further comprises connection means (25) arranged to receive the external reservoir (R). In accordance with a fourth illustrative non-limiting embodiment of the present invention, the second non-limiting embodiment is further modified so that the reservoir is an internal reservoir (13R) integrated into the volatile liquid droplet dispenser device.

In accordance with a fifth illustrative, non-limiting embodiment of the present invention, the first, second, third, and fourth embodiments are further modified so that the first substrate (11) has a recess in a first main surface (11b), which constitutes a space (13) for containing the liquid substance. In accordance with a sixth non-limiting, illustrative embodiment of the present invention, the fifth non-limiting embodiment, as modifying the fourth non-limiting embodiment, is further modified so that the space (13) is arranged to contain the internal reservoir (13R). In accordance with the seventh non-limiting illustrative embodiment of the present invention, the fifth non-limiting embodiment is further modified so that the first substrate (11) further has a through hole traversing the recess and the other main surface (11a) of the first substrate, and wherein the liquid outlet means (14) are arranged in the through hole so as to delimit the recess in the first main surface (11b) thus closing the through hole. According to an eighth non-limiting illustrative embodiment of the present invention, the first, second, third, fourth, and fifth non-limiting embodiments are further modified so that the actuating membrane (31) is arranged in between the first and second substrate (11; 12) and delimits the space (13).

In accordance with a ninth non-limiting illustrative embodiment of the present invention, the first, second, third, fourth, fifth, sixth, seventh and eighth non-limiting embodiments are further modified so that the liquid outlet means (14) has a nozzle body including a thicker main section (14a) and a thinner membrane section (14b), wherein the thinner membrane section comprises the at least one outlet nozzle (14c). In accordance with a tenth non-limiting illustrative embodiment of the present invention, the first, second, third, fourth, fifth, sixth, seventh and eighth non-limiting embodiments are further modified so that the liquid outlet means (141, 142) consists of a flat substrate comprising the at least one outlet nozzle. In accordance with an eleventh non-limiting illustrative embodiment of the present invention, the first, second, third, fourth, fifth, sixth, seventh, eighth, ninth, and tenth non-limiting embodiments are further modified so that the volatile liquid droplet dispenser device further comprises a programmable microcontroller (30) for controlling the actuating membrane (31) by varying its operating frequency, and by varying its power supply, wherein the operating frequency range and supply voltage are chosen to correspond to a range of viscosities and a particular droplet size.

In accordance with a twelfth non-limiting illustrative embodiment of the present invention, the first, second, third, fourth, fifth, sixth, seventh, eighth, ninth, tenth and eleventh non-limiting embodiments are further modified so that the fluidic channel is a wick (13c). In accordance with a thirteenth non-limiting, illustrative embodiment of the present invention, the first, second, third, fourth, fifth, sixth, seventh, eighth, ninth, tenth and eleventh non-limiting embodiments are further modified so that the fluidic channel is a metal plate (15b). In accordance with a fourteenth non-limiting illustrative embodiment of the present invention, the first, second, third, fourth, fifth, sixth, seventh, eighth, ninth, tenth and eleventh non-limiting embodiments are further modified so that the fluidic channel contains a plurality of micro-channels (13c) arranged in the first main surface (11b) of the first substrate. In accordance with a fifteenth non-limiting illustrative embodiment of the present invention, the first, second, third, fourth, fifth, sixth, seventh, eighth, ninth, tenth, eleventh, twelfth, thirteenth and fourteenth non-limiting embodiments are further modified so that the fluidic channel also constitutes a buffer reservoir (132c).

In accordance with a sixteenth non-limiting, illustrative embodiment of the present invention, the first, second, third, fourth, fifth, sixth, seventh, eighth, ninth, tenth, eleventh, twelfth, thirteenth, fourteenth and fifteenth non-limiting embodiments are further modified so that the liquid inlet means is a wick (41, 411, 412). In accordance with a seventeenth non-limiting illustrative embodiment of the present invention, the first, second, third, fifth, seventh, eighth, ninth, tenth, eleventh, twelfth, thirteenth, fourteenth, fifteenth and sixteenth non-limiting embodiments are further modified so that the liquid inlet means (41) is a solid tube arranged to extend into the external reservoir (R). In accordance with an eighteenth non-limiting, illustrative embodiment of the present invention, the first, second, third, fourth, fifth, sixth, seventh, eighth, ninth, tenth, eleventh, twelfth, thirteenth, fourteenth, fifteenth, sixteenth, and seventeenth non-limiting embodiments are further modified so that the actuating membrane (31) is formed of a first part and a second part that are arranged in a slideable arrangement with respect to each other.

In accordance with a nineteenth non-limiting, illustrative embodiment of the present invention, the first, second, third, fifth, seventh, eighth, ninth, tenth, eleventh, twelfth, thirteenth, fourteenth, fifteenth, sixteenth, seventeenth and eighteenth non-limiting embodiments are further modified so that the external reservoir (R) comprises a collapsible bag linked to the liquid inlet means (41). In accordance with the twentieth non-limiting, illustrative embodiment of the present invention, the first, second, third, fourth, fifth, sixth, seventh, eighth, ninth, tenth, eleventh, twelfth, thirteenth, fourteenth, fifteenth, sixteenth, seventeenth, eighteenth and nineteenth non-limiting embodiments are further modified so that the volatile liquid droplet dispenser device further comprises a venting means (13d, 141a, 142a). In accordance with a twenty-first non-limiting, illustrative embodiment of the present invention, the twentieth non-limiting embodiment, as modifying the eleventh non-limiting embodiment, is further modified so that the programmable microcontroller (30) is further arranged to actuate the actuating membrane in a bubble-eliminating mode for driving any air bubbles contained in the liquid substance towards the venting means (13d, 141a, 142a) by applying bursts at a frequency of a few to several times higher than the normal operating frequency and with a duration from under 1 second to several seconds.

In accordance with a twenty-second non-limiting, illustrative embodiment of the present invention, an apparatus is provided that comprises a volatile liquid droplet dispenser device according to any one of the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth and twenty-first non-limiting embodiments. In accordance with a twenty-third non-limiting illustrative embodiment of the present invention, the twenty-second non-limiting embodiment is modified so that the apparatus is a vacuum-cleaner, a floor cleaner, robotics to clean a room, an aromatherapy apparatus, a respiratory therapy apparatus, an air-freshener, a fragrancer, an air purifier, an air conditioner, an insecticide dispensing apparatus, an ironing machine, a white goods appliance or an individual communication apparatus.

Thanks to the construction of the innovative and inventive dispenser device according to the present invention an efficient device fulfilling these objectives in various embodiments may be obtained in a relatively simple and inexpensive manner.

Furthermore, due to the specific design of the device according to the present invention, in particular the eccentric decoupling of the liquid inlet and outlet means and the relative positions of the liquid inlet and outlet means, it is possible to easily exchange the reservoir without any unwanted spill or wastage of liquid contained in the reservoir.

Furthermore, due to the specific outlet means and delivery control method of the device, it is possible to introduce innovative coordinated and remote control features for a variety of liquids while maintaining the other advantages of avoiding passive evaporation, olfactory fatigue and fall-out.

Furthermore, these micro-fluidic characteristics can be complemented by equally innovative electronic circuitry, which aid in expanding the functional capabilities of the device according to the present invention.

BRIEF DESCRIPTION OF THE DRAWINGS

Other features and advantages of the liquid droplet spray system according to the present invention will become clear from reading the following description, which is given solely by way of a non-limitative example thereby referring to the attached drawings in which.

DETAILED DESCRIPTION OF THE INVENTION

Examples of preferred embodiments will now be described.

Figure 1A:
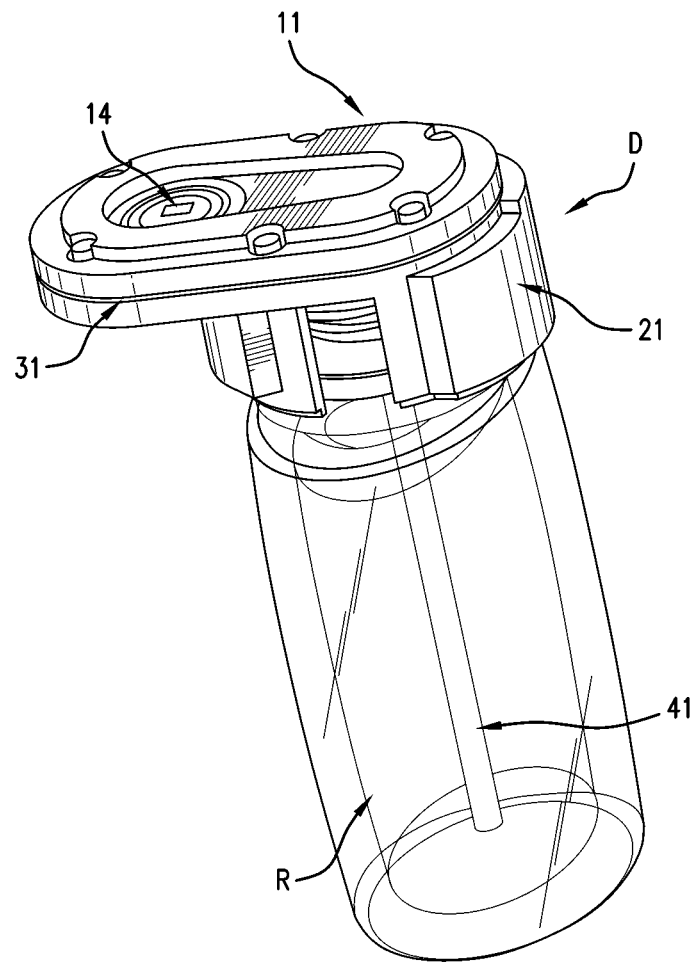
FIGS. 1a, 1b (1bI and 1bII) and 1c (1cI to 1cIV) show examples of a volatile liquid droplet dispenser according to the present invention.

FIG. 1a shows a volatile liquid droplet dispenser according to a first preferred embodiment of the present invention indicated by general reference D. This dispenser comprises a dispenser device 1 and an external, disposable reservoir R as well as electronic circuitry and power supply means (not shown). Volatile liquid dispenser device 1 comprises a first, top substrate 11, and a second, bottom, substrate 21, an actuating membrane 31, arranged between the first and second substrates 11, 21 and containing an electrode membrane, not shown in this figure, for supplying electric power to the actuating membrane 31. Reservoir R in this case contains a functional liquid such as an air freshener liquid that is supplied to a space between the first and second substrate as will be explained later. Such reservoir can be external and of the disposable refill type or internal for very small quantities in the order of less than 1 ml or less than a few ml for example. In the case shown in FIG. 1a, the liquid supply to an external reservoir R is assured by a wick 41. The liquid supply point puts the top of the wick substantially at the same height or slightly higher than the space between the first and second substrate, but eccentrically with regards to liquid outlet means 14 as will be shown further on. The liquid may be expelled as a controlled droplet spray from the volatile liquid dispenser device D when the reservoir is connected thereto. Applicant has found that aqueous liquids function very well with this configuration.

Figures 1, 1B:
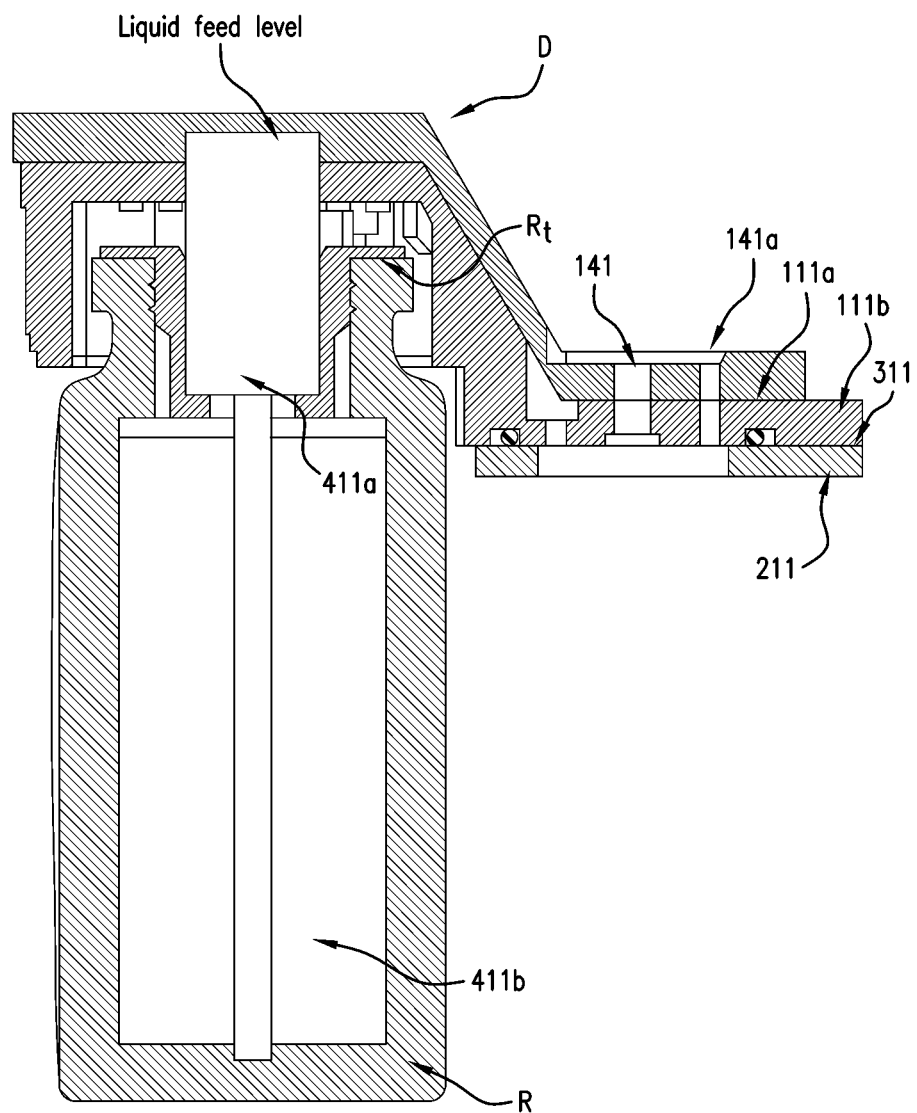

FIG. 1bI shows another embodiment of the volatile liquid droplet dispenser according to the present invention that might be more suitable for other functional liquids like air freshening or other fragrances. In this device, the first, top substrate 111 consists of 2 parts, 111a and 111b, which can be manufactured as one single part. The liquid is supplied in this case by a dual wick 411a and 411b to a space between the first and second substrate as in the previous embodiment and as will be explained later. Top substrate 111 is shaped to position the top of wick part 411a, and hence the liquid feed point, well above the reservoir top $R_t$. Top substrate part 111a is further shaped with a downward inclination providing a slight overpressure with regards to liquid outlet means 141. This overpressure is advantageously chosen not to overcome the oozing pressure of outlet means 141 and vent 141a so as to maintain the advantage of keeping the liquid inside the dispenser when not actuated. As known in the art, vent 141a can be fitted with hydro- or oleophobic or anti-microbial material as required by the application. The level of the space between top substrate part 111b and actuating membrane 311 arranged between the top substrate and bottom substrate 211 at the point of liquid outlet means 141 is now at the level of the liquid when the reservoir R is full. As will become evident from FIG. 1bII, such an innovative arrangement, in addition to the eccentric liquid inlet versus outlet arrangement, a substantially elevated liquid entry point and an advantageous positioning between reservoir liquid level and outlet means, allow for better emptying of a given reservoir R for a larger variety of liquid properties compared to cited prior art and even to the first preferred embodiment described in FIG. 1a. FIG. 1bII indeed explains the fluidic principle including the various heights which determine the liquid feed performance as a function of liquid density and gravity for given capillaries, as the person skilled in the art will readily understand.

Figures 1, 1B, 2:
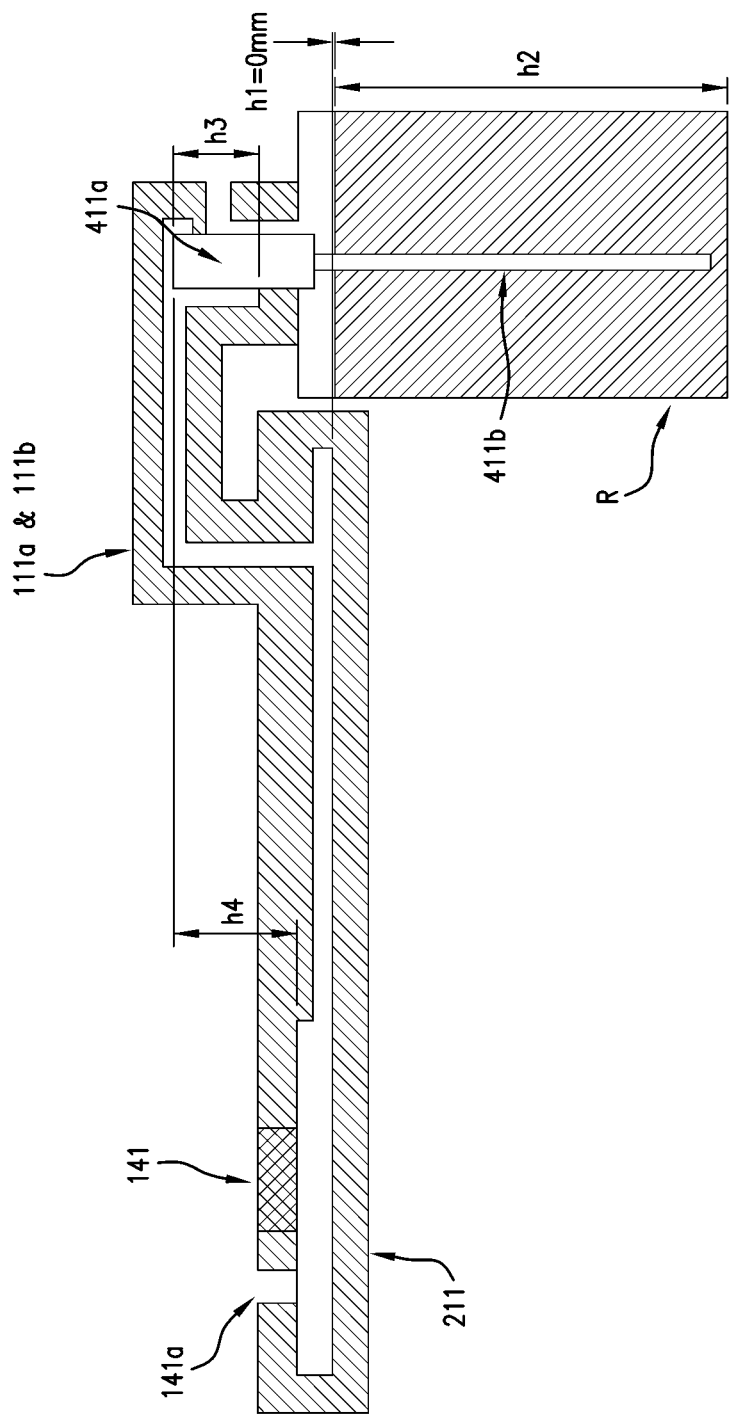
Figures 1, 1C:
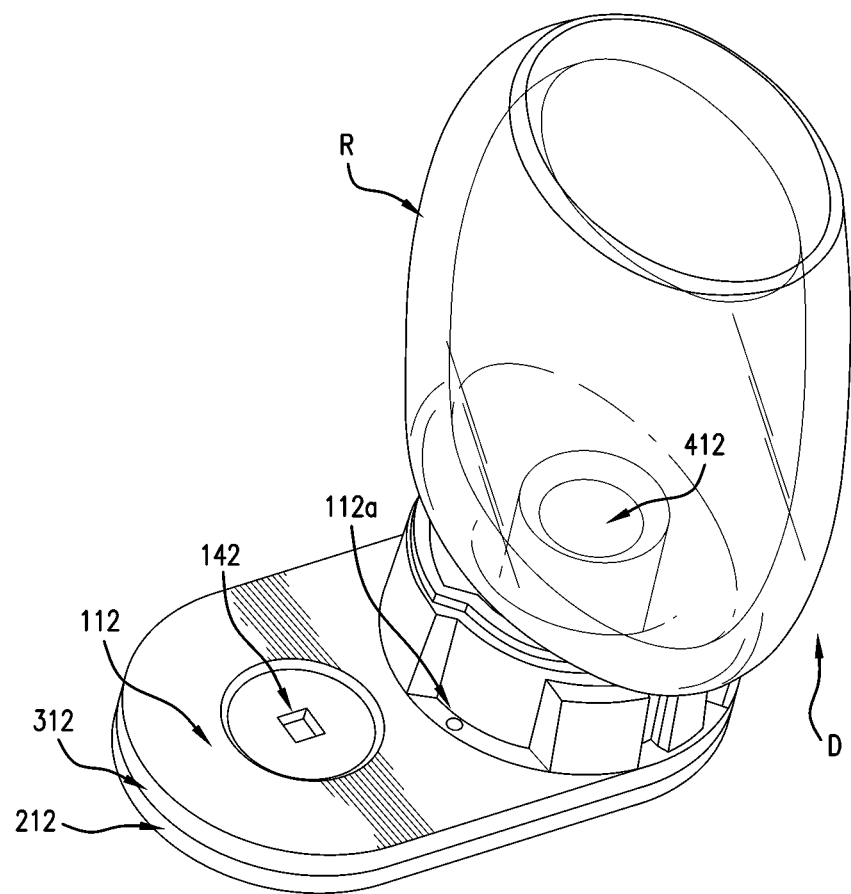
Figures 1, 1C, 2:
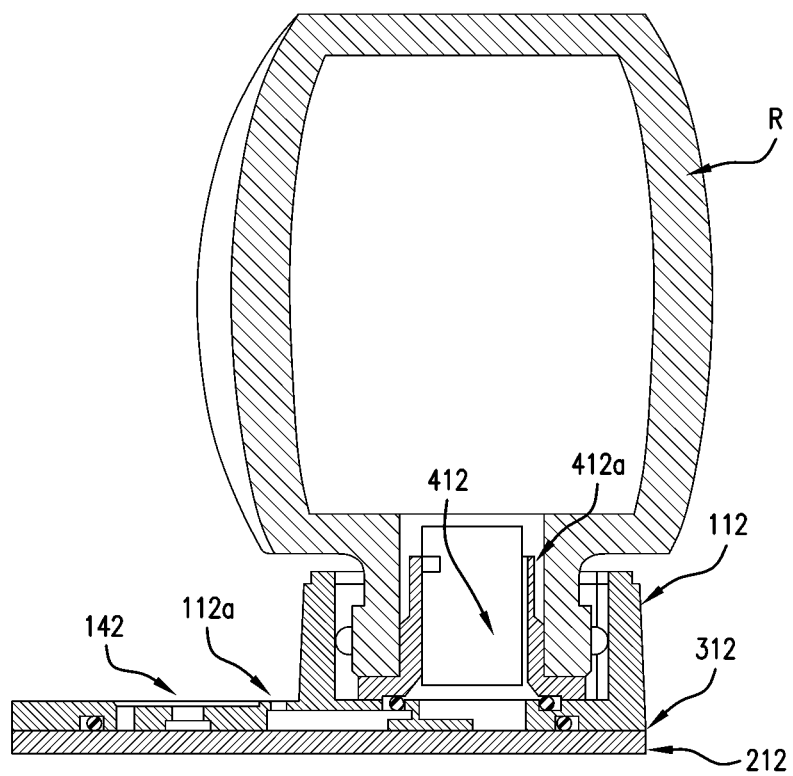
FIG. 2a shows a first substrate of a volatile liquid dispenser device according to the example shown in FIG. 1a of the present invention.
FIG. 2b shows a further example of a first substrate of a volatile liquid dispenser device incorporating an internal reservoir.

FIGS. 1cI and 1cII show yet another embodiment of the volatile liquid droplet dispenser according to the present invention, an upside down version in this case, which might be suitable for a large range of functional liquids. As can be seen from this drawing, the liquid enters from the up side down reservoir R through a liquid entry point located now in the first, top substrate 112 by way of a liquid dosage component, for example a wick 412, as shown here, or another dosage component such as a septum-needle arrangement or an active or passive valve. Reservoir R is vented through the liquid dosage component as is well known in the art via vent 412a and top substrate 112 may equally be vented as shown with venting means 112a and 142a. For medical or other sensitive applications, the venting means 112a and 142a may be executed as anti-microbial filters that are available in suitable materials and shapes. It can easily be imagined that Reservoir R is an external part as shown in the FIGS. 1cI to 1cIV or be partially integrated into top substrate 112 as an additional volume. Such volume can be constituted by enlarging recessed portion 13 within inside surface 11b as shown in FIG. 2b where numeral 13R indicates an internal reservoir and by closing aperture 31c in actuating membrane 312 shown in FIG. 8a. The reservoir function will be completed by joining top substrate 112, actuating membrane 312 and bottom substrate 212 as shown for the other embodiments and hence closing of the additional volume in substrate 112 to form an internal reservoir. The internal reservoir can be pre-filled or refillable from the outside through well known suitable means such as shown for example in FIG. 2b with filling aperture 13F and closed off with a plug, cap or septum and the like (not shown). Liquid outlet means 142 are located in top substrate 112 and connected to a space between the top substrate and actuating membrane 312 arranged between the top substrate and bottom substrate 212 as explained for the previous embodiments and as will be shown in detail in further figures.

FIGS. 1cIII and 1cIV show the basic working principle. The pressure inside the space between top substrate 112 and actuating membrane 312 as said above will be related to liquid density, to gravity and the liquid heights h1 and h2 as well as to the oozing pressure determined by the nozzle density and the nozzle diameter of the outlet means 142 as explained for outlet means 14, 141 and 142. The height h1 inside the lateral liquid feeding part between the eccentric liquid inlet and outlet will be advantageously chosen not to overcome the oozing pressure of liquid outlet means 142 as explained for the previous embodiment. Depending on liquid outlet means 142, the oozing pressure will be less than or equal to 5 mbar, for example for air freshener applications. Other applications might have different oozing pressures. As the person skilled in the art will notice, height h2 will change with variations of liquid density due to ambient temperature variations.

FIGS. 1cIII and 1cIV relate to two configurations of this preferred embodiment with the key difference being in the differing liquid heights h1 inside the lateral liquid feeding part between the eccentric liquid inlet and liquid outlet. In a dynamic state, during a spray cycle for example and as shown, h2 becomes equal or smaller than h1 and there is air intake from vent 112a in top substrate 112 to Reservoir R via vent 412a. Since spray times in most applications are very small, typically from a few milliseconds to 1 second, and the sprayed volumes range from a few nanoliters to a few microliters, this air intake is hardly noticeable. As will become clear from this description, the key advantage of this preferred embodiment of the volatile liquid droplet dispenser above and beyond the innovations of the two previous embodiments, is an increased freedom of the reservoir size and wick length, while maintaining all the other advantages.

After this general description of the preferred embodiments, further details will be described as shown in the following figures. For the sake of clarity, the following Figures and their details will first be selected and discussed in the order of those components which are directly related to the first preferred embodiment according to FIG. 1a. Thereafter the details referring to constructional differences between the described preferred embodiments will be explained as related in the ensuing figures and then will follow the description of the electronic features according to the present invention.

Figure 2A:
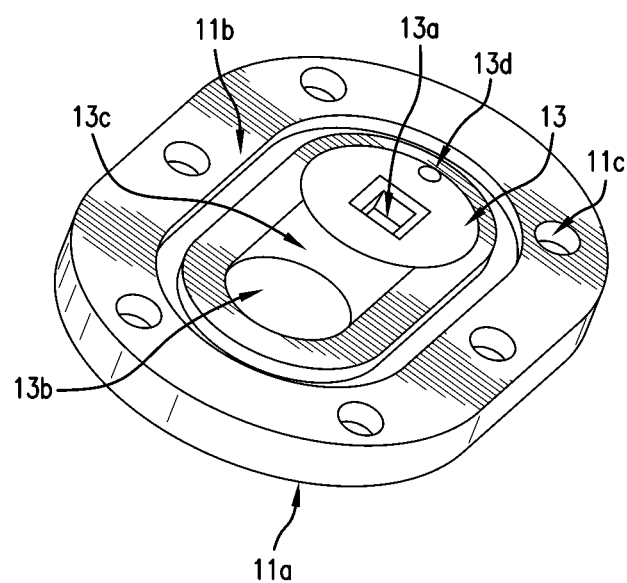
Figure 2B:
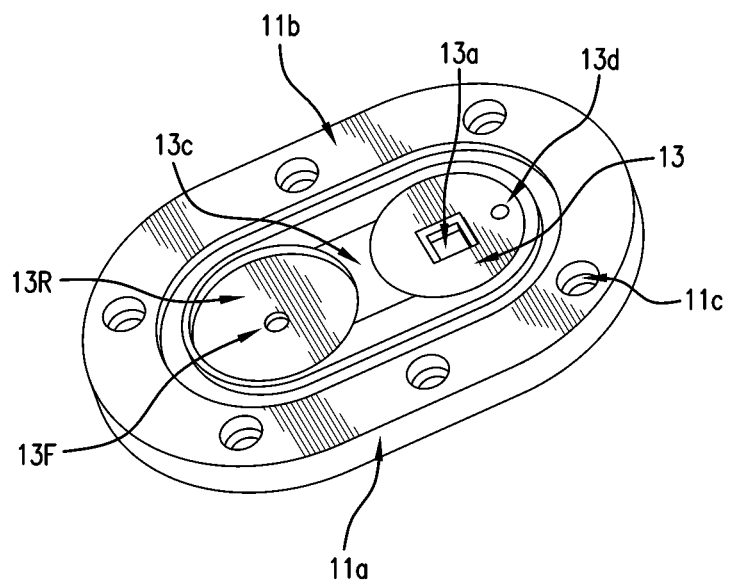
Figure 3:
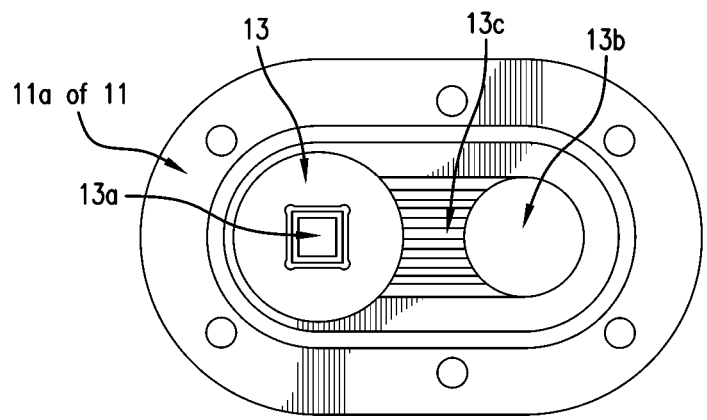
Figure 4:
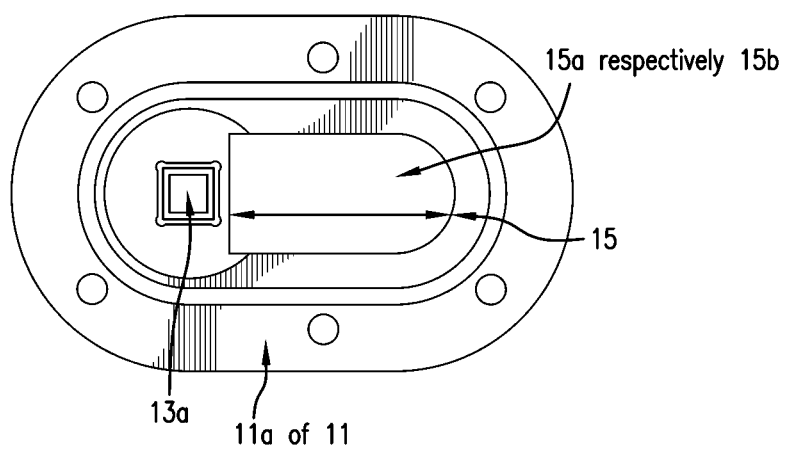
Figure 9A:
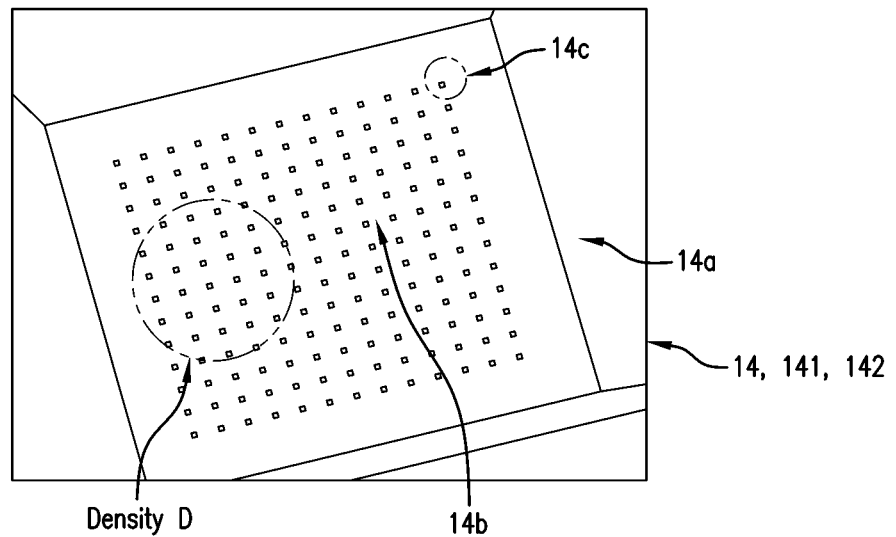
FIG. 9 shows an example of the outlet means for assembly in any of the variants of the first substrate.
Figures 9B, 9C:
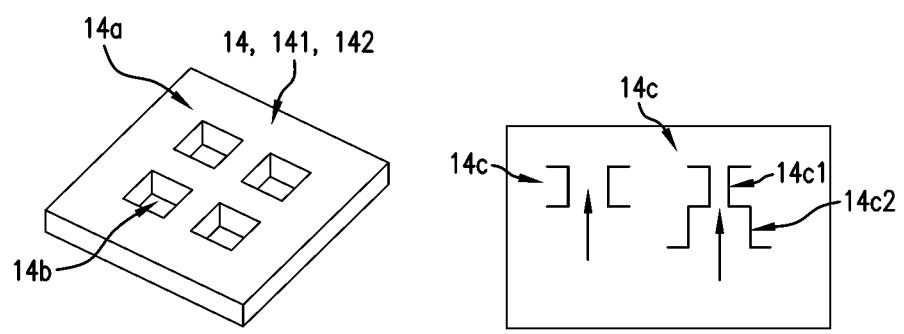
Figure 10:
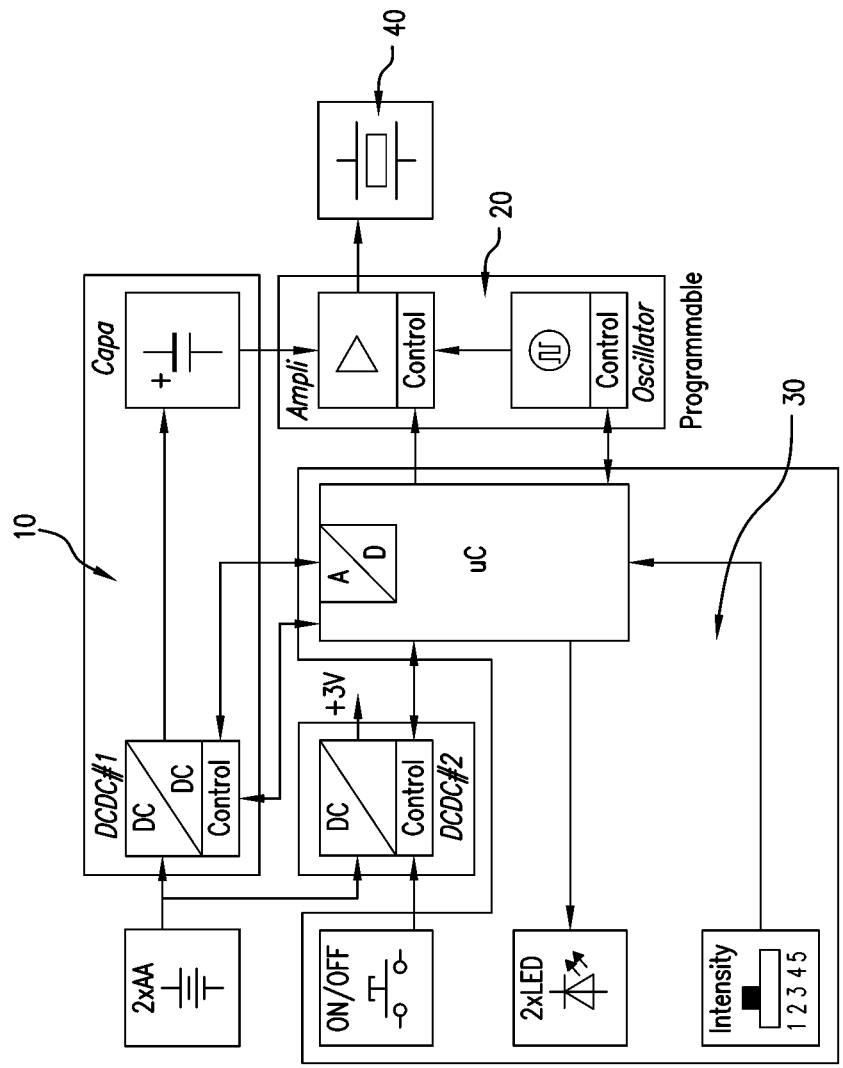
FIG. 10 shows an example of the electrical schematic for a volatile liquid dispenser device according to the present invention.

FIG. 2a shows a top view of an example of a first substrate 11 of the volatile liquid dispenser device 1 according to FIG. 1a of the present invention and explains the principle of eccentricity common to the preferred embodiments. First substrate 11 has an outside surface 11a (not shown) and an inside surface 11b, as shown in FIG. 2a. Inside surface 11b has a recessed portion 13 which constitutes a space for receiving the liquid substance from the external reservoir, as will be explained in more detail later. The space is important for all embodiments to reach a first objective of the invention, which relates to limiting passive evaporation and thus olfactory fatigue. In this embodiment, the liquid is supplied to space 13 laterally by capillarity within substantially the main horizontal plane. Since the capillary pressure which supplies the liquid laterally into the space is not high enough to overcome the adhesion forces between the liquid and the substrate material, hence the oozing pressure of the liquid outlet means 14, the liquid remains inside when the device is not activated and the combined open surface of the nozzles, the only surface available for evaporation of the volatile liquid is very small compared to the internal surface of the space. The ratio can be as small as 1.8E-5 depending on the nozzle diameters and density. Applicant has experienced passive evaporation values with prototype devices during 24 hours, which are about 10% of other cited piezo-electric devices and incomparably less than in prior art open wick type devices. A venting channel, (not shown) and an opening 13a are further provided within the first substrate 11 for locating the liquid outlet means 14 of which an example is shown in FIG. 9 and which is common to all embodiments, 141 for FIG. 1b and 142 for FIG. 1c.

Liquid outlet means 14 may be constituted by one or more apertures. As shown in FIG. 9, for example, liquid outlet means 14 may be formed of a nozzle array made out of silicon, a polymer, a resin such as SU-8, Nickel, Parylen or any suitable material or combination of materials that allows for a sufficiently precise and cost-effective manufacturing of the outlet nozzle array. For example, a higher precision process, like ICP (Inductively controlled plasma etching), SU-8 spin coating, irradiation and development as well as proton or ion beam machining, may be used for manufacturing the nozzle part of liquid outlet means 14 than for the other parts which are less critical for fluidic performance. The outlet means consists of a substrate having one or more thicker portions 14a, also called the reinforcement portions, and thinner perforated membrane portions 14b as shown in FIGS. 3a and 3b. The perforations constitute liquid outlet nozzles 14c and are provided such that a liquid substance may exit the space positioned below through liquid outlet means 14 and the volatile liquid dispenser device by traversing the one or more perforations of the perforated membrane. Outlet means 14 is thus fitted into opening 13a to complete the first substrate 11. Perforate membrane 14b may be made for instance as a nozzle array containing for example 64, 128 or more outlet nozzles 14c per thinner membrane portion 14b. Such outlet means are known as such, see for example the document EP-A-0 923 957 and EP 1 273 355 in the name of the present Applicant. The properties of this arrangement and the other components of the innovative volatile liquid droplet dispenser allow to overcome most of the problems not addressed by prior art devices as will be shown further on. As is known from the prior art introduced by the same applicant and shown in FIG. 3c, the liquid outlet means may comprise straight walled channels 14c with a constant diameter and an immediate nozzle outlet or may comprise stepped channels with a given channel diameter 14c 2 and a reduced diameter nozzle outlet 14c 1.

As is known to the person of the art, the diameter variations are related to accommodating physico-chemical properties as well as energy conversion factors to obtain an optimal spray for a given energy input. As is further known to the person skilled in the art, by varying the number of outlet nozzles, the quantity of liquid to be expelled from the device may also be varied. But, in fact as the amount of nozzles increases in the nozzle array, the resulting total pressure drop decreases, so tuning the resulting pressure drop via the nozzle density D is another of the innovative features of the device. Hence by changing the nozzle density D (see FIG. 3a) the innovative device is able to accommodate for different viscosities. For example by increasing the nozzle density D from say 85 to 169 nozzles per thinner membrane section 14b, the device reacts to a given viscosity, applying for example to an aqueous liquid and while keeping the same nozzle diameter, to change from emitting droplets in the 3 to 4 micrometer range to emitting droplets in the 10 to 20 micrometer range and correspondingly to deliver much higher flow rates. On the other hand, for a viscosity of a liquid suitable for an air freshening liquid, the higher of the two mentioned nozzle densities D can still be used to produce droplets in the 3 to 4 micrometer range and a higher flow rate than the lower of the two mentioned densities D.

As can be understood by the person skilled in the art, this effect could of course also be obtained in another manner, by simply increasing the nozzle diameter. But nozzles with a larger diameter facilitate leakage, resulting in larger droplets and the corresponding problems of less efficacy, higher fall-out and less efficient evaporation. On the other side, higher density nozzle arrays are smaller, hence less expensive.

By opting for a straight or stepped channel, hence tuning the individual pressure drop to the application as compared to the tuning of the total pressure drop as discussed above, the two effects can now be combined to adapt the innovative device to the physico-chemical properties of the liquid. For example, liquids of a higher viscosity can be sprayed with small diameter droplets if the density D (See FIG. 3a) is increased, if the nozzle length 14c is reduced or if the proportions 14c 1 and 14c 2 of a stepped nozzle are modified. This can compensate for the effect that the higher pressure drop corresponding to small nozzle diameters is increased even further by a higher viscosity and a longer nozzle channel which might finally prevent the device from spraying.

As is obvious from the FIGS. 1a, 1b, 1c and 9, the liquid outlet means 14, 141, 142 are identical and apply in their functionality to all and any of the preferred embodiments, same as opening 13a, 131a and 132a in the corresponding top substrates 11, 111 and 112. As can be understood by the person skilled in the art, using the innovative concept of liquid outlet means 14 according to FIG. 9 allows novel applications in the field as represented by the previously described preferred embodiments when compared to the typically tapered shape nozzles of standard vibrating orifice devices.

Figure 7A:
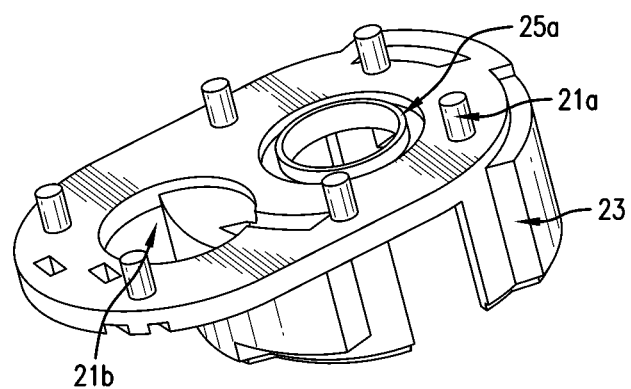
FIG. 7 shows a second substrate of a volatile liquid dispenser device according to the example shown in FIG. 1a of the present invention.
Figure 7B:
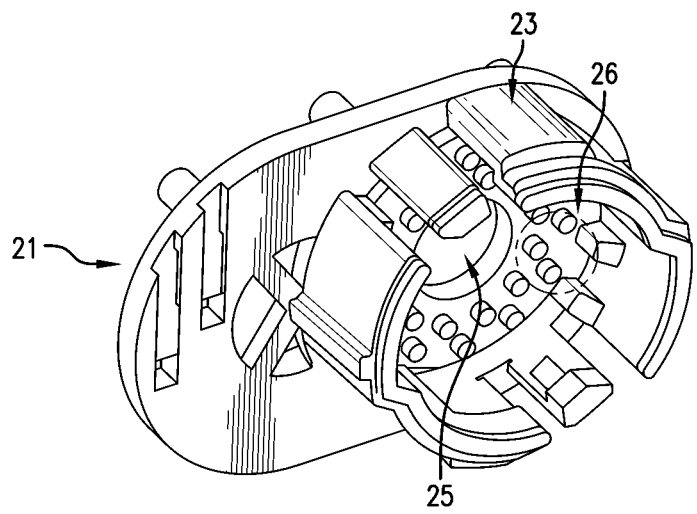

FIG. 7 shows two views of the second substrate 21 according to the preferred embodiment described in FIG. 1a. Second substrate 21 comprises connection means 23 for connection to an external reservoir containing a volatile liquid that is to be dispensed. In this case, connection means 23 is of the screw-type having a partial inner thread for receiving the reservoir by twisting the latter into the partial thread. Further, an aperture 25a for accommodating liquid inlet means are provided in second substrate 21 for allowing the liquid substance to enter the volatile liquid droplet dispenser device 1 from the external reservoir R. Such means are in themselves not inventive but may be a passive pump, for example, a wick made a soft porous medium, that enters the reservoir to allow for extraction of the liquid into the device. Such means can also be an active pump which has a tubular rod for extending into the reservoir via a dip-tube and which pumps the liquid out of the reservoir. Such pump may be a micro-pump as described in document EP-A-0 641 934, in the name of the present Applicant, an other micro-pump such as a membrane or small displacement peristaltic pump, an osmotic pump and the like. In such a case, electrical and electronic pump actuating means may be provided on the device to trigger the pump, thus causing the liquid to be sprayed to flow through the dip-tube and the rod into the device. This solution may be advantageous for high flow rate, controlled droplet size and sustained flow delivery devices such as medication or para-medication nebulizers, inhaling devices, fine fragrance dispensers, large volume sanitizing or other air care dispensers. Sustained flow delivery may be understood as droplet spraying flows from pulsed flows of preferably more than 100 ms to several seconds and in pulse trains of total durations of seconds to several minutes. This particular feature of the innovative device allows it to be adapted to function as such and to supply the liquid from a flask, a (collapsible) bag or other reservoir directly, via a wick or a dip-tube to a pump and from the wick or the pump to the dispensing device. In the context of the invention, wick and pump are solely representative of passive and active liquid supply means. Indeed, a collapsible bag inside the external reservoir could be used in a wick-less arrangement, in a manner that is well known to a skilled person. Preferably, venting means 26 are provided in the second substrate surrounding the liquid inlet means so as to facilitate the liquid flow from the reservoir into the volatile liquid dispenser device.

As shown in FIG. 7, the wick or rod preferably enters an aperture 25a, i.e. the liquid inlet means, provided in second substrate 21 and extends slightly beyond the top surface of second substrate so as to allow the liquid to flow into the device, as will be explained in more detail later. The person skilled in the art will recognize that, same as elsewhere in the description, discrete or bi-injection moulded gaskets are provided where needed and are not shown in the drawings for reasons of simplicity.

As can also be seen in FIG. 7, several protrusions 21a are provided for assembling the second substrate to the first substrate by aligning the protrusions with appropriate holes 11c in the first substrate (see FIG. 2a) for joining by ultrasonic welding. Of course, other means for assembling the device may be used instead, such as co-injection, gluing or the like.

Figure 5A:
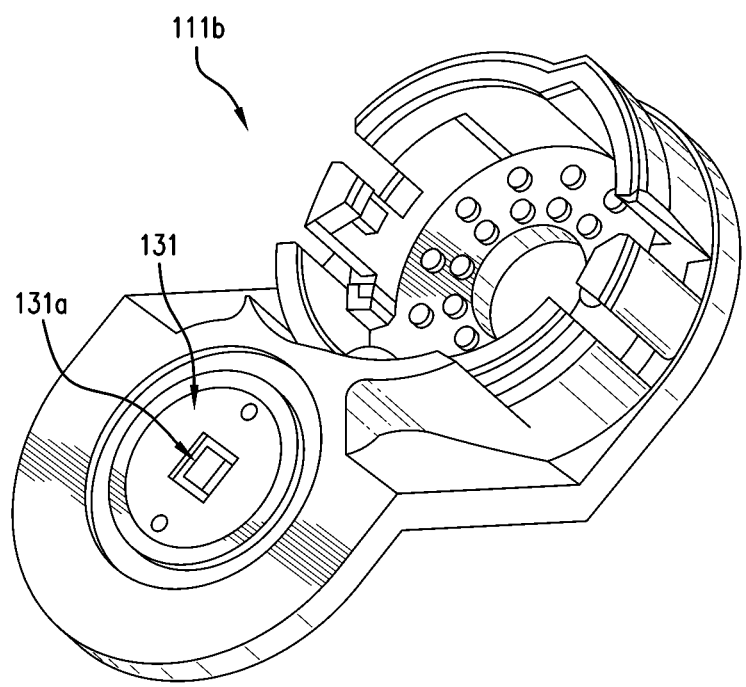
Figure 5B:
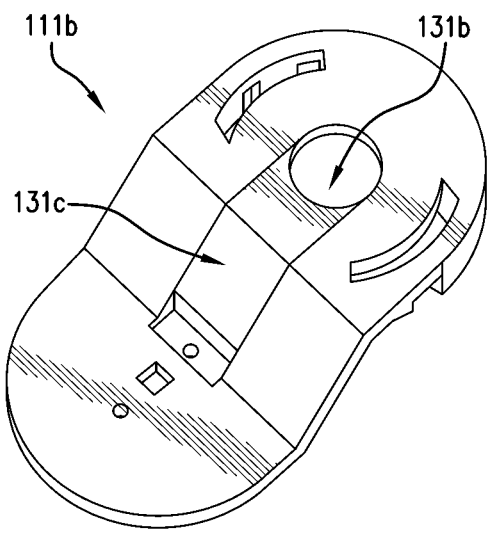
Figure 5C:
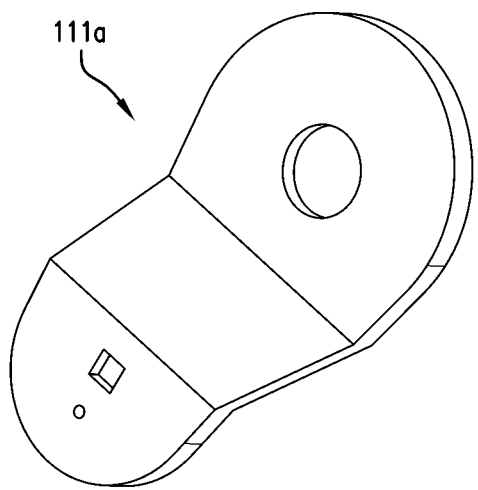

The above features related to the bottom substrate 21 as disclosed in the preferred embodiment according to FIG. 1a are also contained in FIGS. 5a and 5b related to top substrate 111 of the preferred embodiment according to FIG. 1b. FIG. 6 relates to the top substrate 112 of the preferred embodiment according to FIG. 1c, which advantageously combines features of both top and bottom substrates resulting in cost reduction advantages.

Figure 8A:
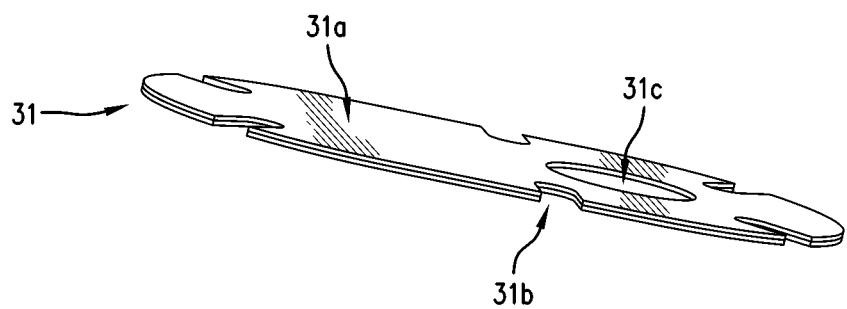
FIGS. 8a and 8b show an actuating membrane of a volatile liquid dispenser device according to the example shown in FIG. 1a of the present invention.
Figure 8B:
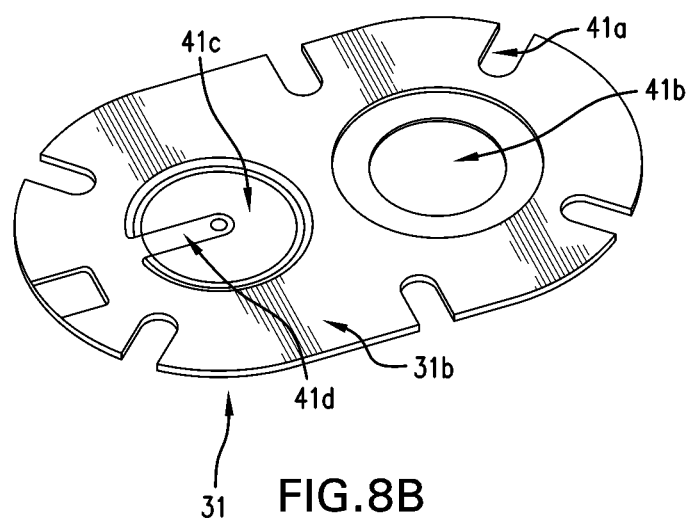

FIGS. 8a and 8b show details of an actuating membrane 31 that is arranged between the first and second substrate in a sandwich-like manner. This actuating substrate itself is constructed as a sandwich, preferably made of metal and polymer as will be shown further on. As shown in FIG. 5a, the upper metal layer 31a has several slots 31b for alignment with protrusions 21a when assembling the device. An aperture 31c is also provided for alignment with aperture 25 of second substrate 21 to allow a wick to pass there through for transportation of liquid.

According to FIG. 8b, actuating membrane 31 is actuated by piezo-electric means that are provided so as to act on the liquid inside space 13 to cause the liquid to undergo vibration and to be expelled as a spray of droplets through the outlet means 14 arranged in first substrate 11. In the shown example, the piezo-electric means are arranged in the actuating membrane, as will be explained in more detail hereafter. It should be noted that this is simply an example, and that the piezo-electric means may instead be arranged around the liquid outlet means. In such a case, the piezo-electric mans is preferably circular to surround the outlet means.

To this effect, the actuating membrane sandwich 31 additional to the upper metal layer 31a further comprises an insulating layer (not shown) preferably made out of a polymer and a lower metal layer 31b shown in FIG. 8b. The person skilled in the art will realize that the insulating layer may not need to be a physical foil but a specifically applied insulating surface treatment where necessary and useful. FIG. 8b actually shows the underside of the actuating membrane sandwich, repeating aperture 41b and slots 41a. FIG. 8b also shows the piezoelectric vibrating element 41c which is provided to actuate this membrane 31, which is aligned with and arranged below space 13 and which has a second electrical contact with a contacting electrode 41d. In the case of FIG. 8b, the vibrating element 41c may be contacted from both or from one side only as the person skilled in the art will appreciate. The person skilled in the art will realize that the upper metal layer 31a may not extend specifically over the entire surface of the actuating membrane 31 but be specifically applied as useful, for example as shown in FIG. 1bI with actuating membrane 311 and second, bottom substrate 211. Generally, the contact may be suitably arranged to be accessible through to the bottom surface of the second substrate 21 in FIG. 1a, substrate 211 in FIG. 1b I and substrate 212 in FIG. 1c II (Connection not shown). To this effect, in FIG. 7 second substrate 21 is shown to have a second aperture 21b, as shown in FIG. 4, that is aligned to facilitate such contacting, a feature that is repeated in the other preferred embodiments as shown respectively.

Thus, as shown in Figures in all embodiments according to FIGS. 1a, 1b, 1c, 2, 3, 5 and 6 first substrate 11, 111 and 112 with space 13, 131 and 132 form together with liquid outlet means 14, 141 and 142 and actuating membrane 31, 311 and 312 a liquid droplet spray device for expelling the supplied volatile liquid substance as a spray of droplets in a manner well known from other devices designed by the present Applicant and as described for example in document EP 1 236 517.

In fact, when assembling for example in the first preferred embodiment according to FIG. 1a, first substrate 11 assembled together with actuating membrane 31 and second substrate 21 will delimit the recessed portion in first substrate 11 thus defining space 13 as well as fluidic channel 13c and a liquid entry point 13b. In this example, the liquid entry point is in fact a wick-receiving section.

Further, the wick, or rod, will not only extend beyond the top surface of second substrate 21, but it will extend through aperture 31a to allow liquid to flow across the top surface of actuating membrane 31 through capillary action so as to fill space 13 with the liquid.

To allow for such flow of liquid, and as has been shown in FIG. 2a, inside surface 11b of first substrate 11 is provided with a fluidic channel 13c. In fact, advantageously, first substrate 11 also comprises a liquid entry point 13b, for example an upper part of the cavity for receiving comfortably, i.e. without excessive compression, the tip portion of the wick, when a wick is used, for connection with the fluidic channel 13c which itself is interconnected with space 13 to ensure fluidic flow from the external reservoir through the wick into space 13. In the case of an internal reservoir for very small quantities partially integrated into top substrate as mentioned before and shown in FIG. 2b, the connection 13c between space 13 and such internal reservoir 13R may be via lateral capillary flow as described below.

Figures 1, 1C, 2, 3:
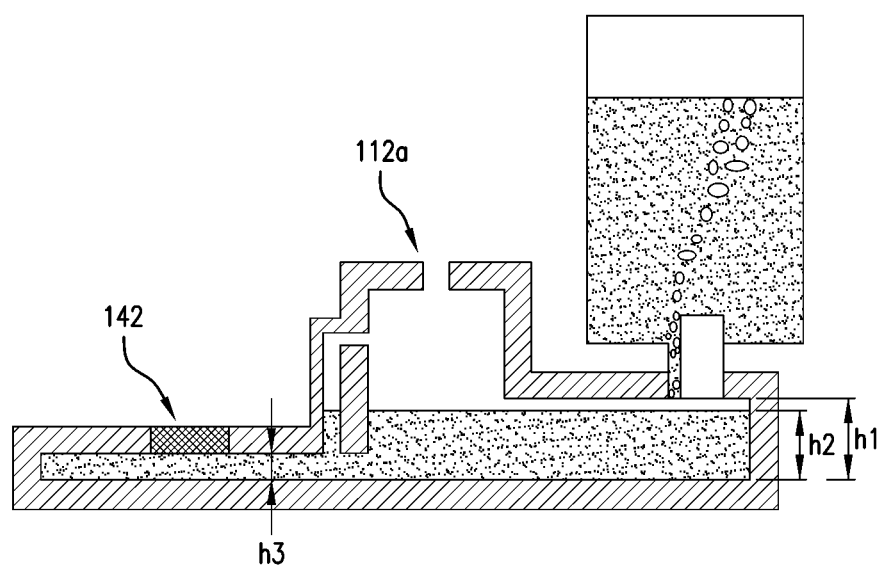
FIG. 3 shows a detailed view of a variant of the first substrate according to the example shown in FIG. 1a of the present invention.
Figures 1, 1C, 2, 3, 4:
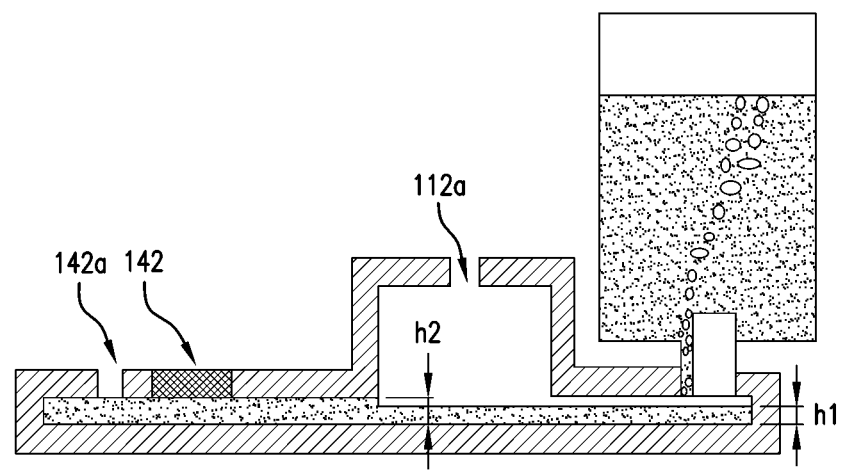
FIG. 4 shows a detailed view of another variant of the first substrate according to the example shown in FIG. 1a of the present invention, FIGS. 5 (5a to 5c) shows a detailed view of a variant of the first substrate according to the example shown in FIG. 1b of the present invention.

FIG. 3 shows an example of first substrate 11. In this preferred embodiment micro-channels 13c are created, for example by plastic injection moulding, within the first main surface 13a of first substrate 11 from the liquid entry point 13b to space 13. In a variant, these micro-channels may extend beyond and into space 13 thus partially or totally being part of space 13.

This fluidic channel thus allows for the lateral capillary flow from the liquid inlet means 25 to space 13, and ultimately to liquid outlet means 14.

FIG. 4 shows another example of the fluidic channel 13c. Here, at least one separate channel 15 is fitted within inside surface 11b of first substrate 11, and thus is sandwiched between the actuating membrane and this first main surface 11a. This separate channel may be a thin, flat wick 15a allowing for the transportation by way of lateral capillary flow of the liquid from the wick tip portion into space 13. Another possibility is to have a metal spacer piece 15b, i.e. a piece of metal, which ensures capillary flow of the liquid from the wick tip portion into space 13. Another possibility is to have the channel injection moulded, same as the micro-channels 13*c* shown in FIG. 6, but essentially more or less flat or low-profiled in cross-section as a function of the liquid to be conveyed. In fact, fluidic channel 13*a* can be tuned to a group of particular volatile liquids to be sprayed as a function of its composition of physico-chemical properties. The effect of this tuning will be mostly directed on ease and speed of priming, e.g. on efficiently filling space 13 for a range of liquids. Filling Space 13, fluidic channel 13*c* and liquid entry point 13*b* are shown in FIGS. 2 and 3 to be substantially in one horizontal plane. However in alternative arrangements, filling space 13 may be located lower than liquid entry point 13*b* in order to maintain an advantageous position with regards to the liquid level in the reservoir R.

The amount of such a gradient applied to the fluidic channel 13 depends on liquid properties like density, surface tension and viscosity and is shown in FIG. 1*b*I and 5*b* respectively. This innovative feature allows the tuning of the micro-fluidic system to a range of particular liquid properties and complete emptying of the reservoir R. Such an arrangement corresponds to a preferred embodiment as shown in FIG. 1*b*.

Figure 6A:
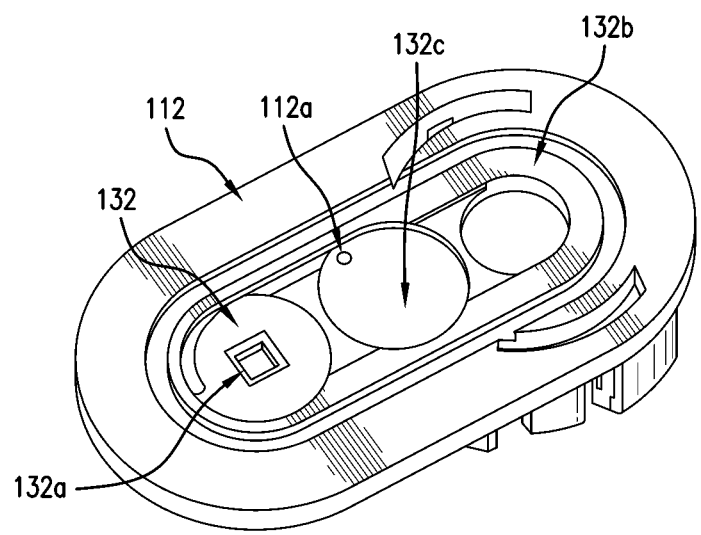
FIGS. 6a and 6b shows a detailed view of a variant of the first substrate according to the example shown in FIG. 1c of the present invention.
Figure 6B:
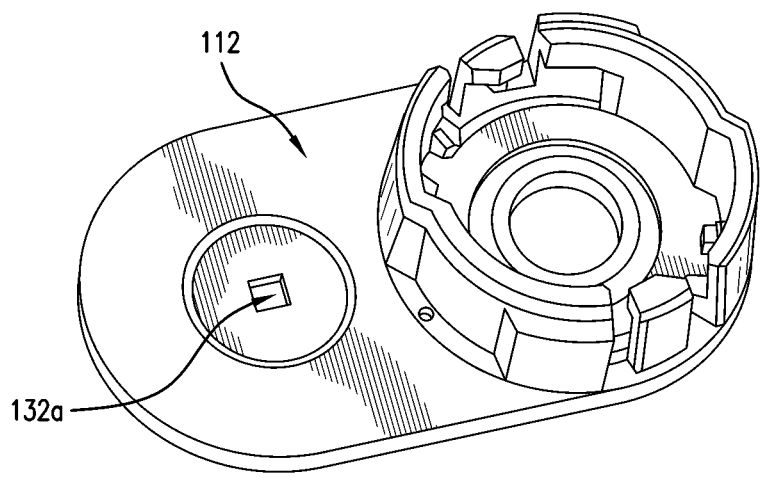

In a further alternative arrangement as shown in FIG. 1*b*I and partially in FIG. 1*a*, a first wick 41 or 411*b* may be pre-fitted in the external reservoir R. The pre-fitted wick will contact a second wick 411*a*, extending through the substrate 21, 111*b* up to the substrate 11,111*a*, so as to connect the first wick to the respective fluidic channels 13*c* 131*c* and 132*c* as shown in FIGS. 1*b*I, 2, 5 and 6. In FIG. 6*a*, fluidic channel 132*c* constitutes a fluidic channel as well as a buffer reservoir according to FIG. 1*c*III and FIG. 1*c*IV. FIG. 6*b* shows the topside of substrate 112.

The piezoelectric element 41*c* is fitted into a suitable aperture like aperture 21*b* in FIG. 7 and thus, when powered, connects electrically to and directly acts on actuating membrane 31, 311 or 312, depending on the respective embodiment, thus causing a vibration on this actuating membrane. This vibration is then transmitted to the volatile liquid in space 13, 131 or 132 thus causing a vibration of and pressure increase within the liquid. As this liquid has nowhere to go but out into the outlet nozzles of outlet means 14, 141 or 142, a spray of droplets will be expelled from the device.

Figure 11A:
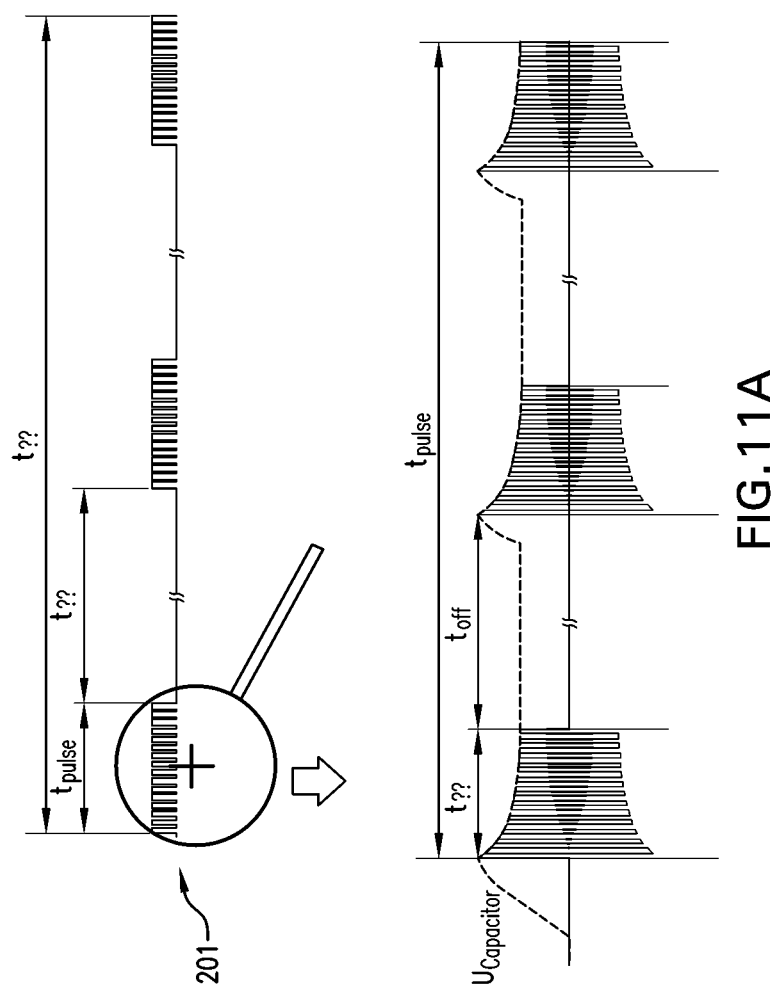
FIGS. 11a and 11b show examples of an actuation mode for a volatile liquid dispenser device according to the present invention.
Figure 11B:
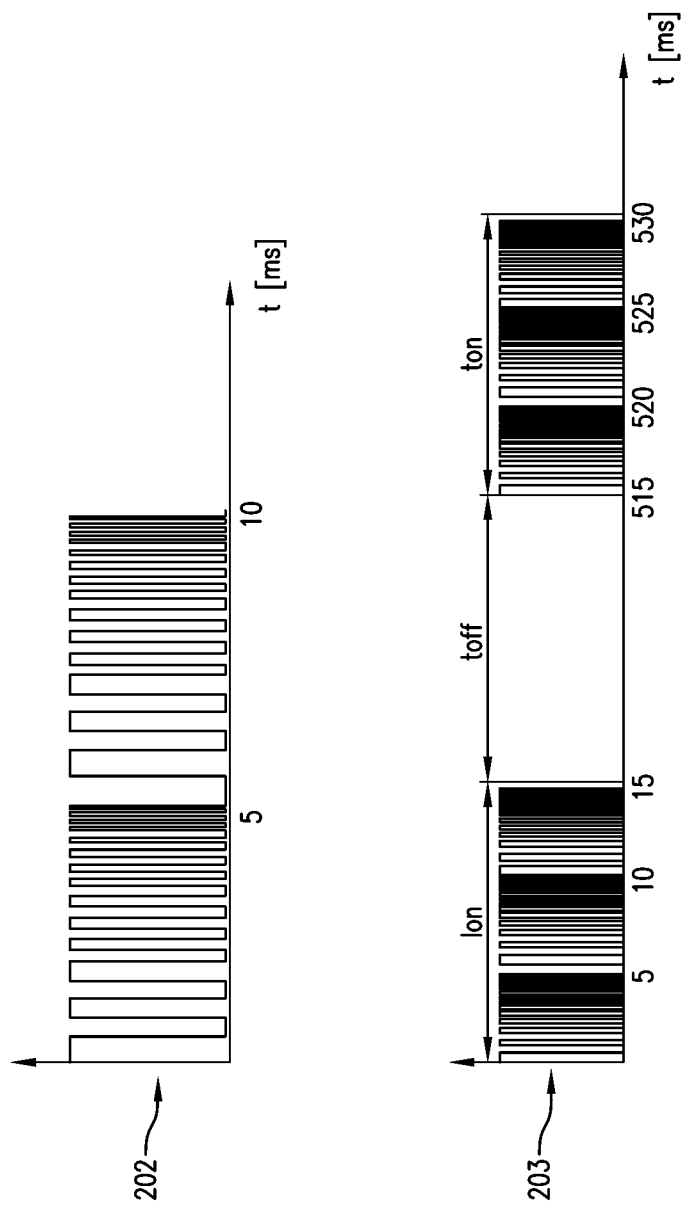
Figure 12:
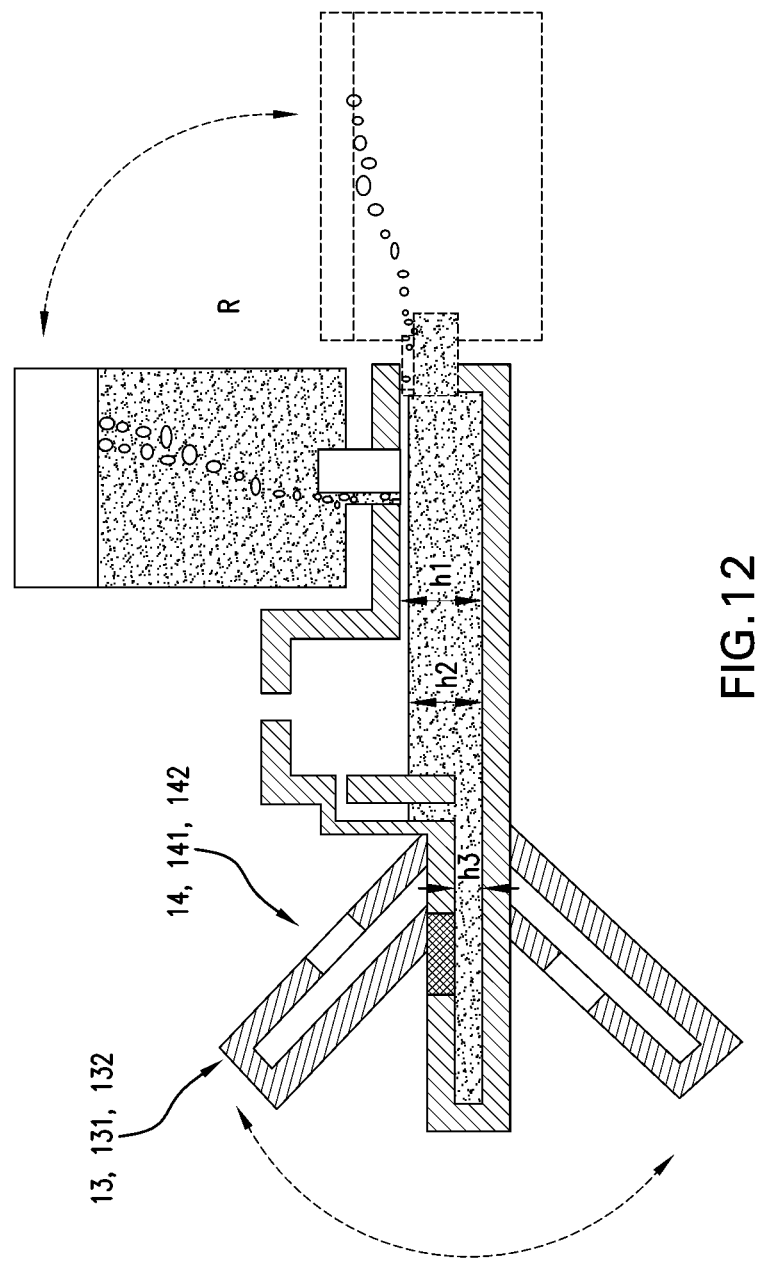
FIG. 12 shows further variants of embodiments of the volatile liquid droplet dispenser according to the invention.

As will be clear to the person skilled in the art different methods of constructing and joining substrates 11, 111 and 112 with actuating membrane 31, 311 and 312 and with substrates 21, 211 and 212 can be implemented while maintaining the innovative features of the device. With regards to the first preferred embodiment according to FIG. 1*a*, it may for example be advantageous to locate a first part of actuating membrane 31 in a permanent housing together with the electronics and the battery, the other second part remaining assembled between substrates 11 and 12. This first part would be for example related to the one carrying the piezo-electric actuator 41*c* as shown in FIG. 5*b*. Both parts of actuating membrane 31, disposable and permanent, may then be connected for example through a sliding arrangement position between otherwise assembled substrates 11 and 21 and secured appropriately. In a similar fashion a further preferred embodiment may feature a fixed bottom substrate 212 joined permanently with the actuating membrane 312 and a sliding, snap-fit or otherwise temporarily fitted top substrate 112. Such an arrangement will be advantageous where top substrate 112 for example including an internal reservoir would be discarded after each use or after several uses as might be necessary for medical applications like nebulizers for example or aromatherapy and other devices equipped to be pre-filled or refillable. This feature would further allow cleaning the actuating membrane after each use or as may be required.

Still other constructive arrangements can be envisioned while maintaining the principle of the invention and the innovative functionality. For example as shown in FIG. 12 and using as an example the schematic known from FIG. 1*c*IV of the present invention, further innovative embodiments can feature Reservoirs R which are fitted laterally in various positions. As also shown in FIG. 12, the volatile liquid dispenser part relating to space 13,131 or 132 and containing liquid outlet means 14, 141 or 142 may be inclined upwards or downwards, as shown in preceding drawings, to accommodate design requests of variants or functional constraints such as space or position and the like.

The innovative fluidic features of the inventive volatile liquid dispensing device now having been explained so far, the electronic control means which further contribute to the objectives of the present invention need to be explained in an appropriate manner. As such driving and controlling means in themselves as shown in FIG. 10, are well known to a person skilled in the art, the explanation will be limited to some of the particular programming aspects of the volatile liquid dispensing device. The programming aspects of the volatile liquid dispensing device will be concentrated on the delivery quality and the energy efficiency of the delivery.

Thus, FIG. 10 shows a power circuit 10 connected to a driver circuit 20 for driving a piezoelectric actuator 40. A (programmable) microcontroller circuit 30 is further provided for controlling the driving of the piezoelectric actuator.

First an electrical power source such as a plug-in module to the mains (not shown) or a battery for powering the electrical control system may be provided in a known manner. Most components shown in FIG. 10, including a programmable oscillator, may actually be integrated into an application specific integrated circuit (ASIC).

FIGS. 11*a* and 11*b* show examples of an actuation mode of the innovative programming means of the volatile liquid droplet dispenser according to the present invention. The person skilled in the art of micro-fluidics will agree that besides using the right fluidic design, the piezo-electric spraying characteristics of liquids depends on using the right amount of energy to respond to different densities and viscosities of liquids in order to correctly pressurize these liquids ultrasonically and to dispense them through a nozzle or a nozzle array in droplets or as a fine mist of droplets.

In a first mode of operation according to FIG. 11*a* or 11*b* and relating to the schematic in FIG. 10, when a battery is put into the device, the capacitor in the power circuit 10 is charged to a voltage of 30 to 60 Volts, preferably to 40 Volts. In one preferred embodiment, when the device is turned on, the capacitor supplies the driver circuit 20 which drives the piezo-electric actuator 40 either in short bursts 201 at a fixed frequency and a variable amplitude as shown in FIG. 11*a*. In another preferred embodiment, the driver circuit 20 drives the piezo-electric actuator 40 in short bursts 202 at a variable frequency and at a constant amplitude as shown in FIG. 11*b*.

In a further preferred embodiment (not shown) driver circuit 20 drives the piezo-electric actuator 40 in short bursts at a variable frequency and a variable amplitude. The programmable oscillator in driver circuit 20 receives the instructions relating to the frequency, the voltage, the ranges and on/off times from the micro-controller circuit 30.

The bursts are in order of several milliseconds or tens of milliseconds according to liquid properties and can be programmed to correspond to a particular fragrance or range of fragrances. In the example of varying amplitude, the capacitor in the power circuit 10 is charged with a constant current during off-time and supplies the driver circuit 20 with a fixed frequency, for example 350 kHz, during a particular burst time. The use of the capacitor further extends battery life and reduces cost of operation. The burst time is chosen and optimised according to the intensity, the sensory performance of a particular fragrance or range of fragrances. In the example of varying frequency the variation is chosen to accommodate variations between liquids, like certain ranges of viscosities, to improve control over the droplet jet and to stabilize the flow rate. The range of frequency variation can be in the order of a few kHz or a few tens of kHz depending on the range of liquid variations to be taken into account. Also as shown in FIG. 11b, the number of bursts 203 or of bursts 201 (see FIG. 11a) can be chosen and optimised according to the individual intensity, the sensory performance of a particular fragrance or range of fragrances. In each case, the intensity over time can be set by either varying the duration of the bursts or of the pauses between the bursts. Total on time can of course also be programmed same as on-time cycles.

In another preferred embodiment several volatile liquid droplet dispensers are arranged together in a multiple dispenser device or another arrangement suited to contain and operate multiple dispensers. In this case, different individual numbers of bursts and frequencies can be selected for different fragrances dispensed by the various devices. The differing numbers, durations and frequencies of bursts can now be used to provide scenting accords corresponding to a mixture of different fragrances and varying sequences thereof and hence to provide an enhanced sensory experience. Of course the accords can be programmed to function in combination with music, moving pictures, light and multimedia applications.

Thanks to the above described features of the present volatile liquid droplet dispenser device, and with an innovative programming of the electronic means, it is further possible to increase the reliability of the device for controlled ejection of a variety of atomised liquid substances. Indeed, as is known in the art, micro-fluidic systems such as described above in the various preferred embodiments dispensing a variety of functional liquids, feature one principal problem impairing dispensing reliability: air bubbles from degassing or other fluidic phenomena. Entrapment of such bubbles can simply not be avoided despite all fluidic engineering, choice of materials, venting and the like such as described in the preferred embodiments above. Hence, the bubbles need to be eliminated at the most critical point which is within space 13, 131 and 132 and in close vicinity of the liquid outlet means 14, 141 and 142.

Applicant has indeed discovered and developed inventive actuation modes of piezo-electric actuator 40 with sequences of actuation and signal characteristics which eliminate such bubbles. Before initiating a sequence of bursts 201, 202 or 203 such as shown in FIGS. 11a and 11b, a bubble eliminating piezo-actuation mode will be initiated which drives the bubbles towards the venting holes 13d, in FIGS. 2a and 2b, 141a, in FIG. 1bI, and 142a, in FIG. 1cIV. This piezo-actuation mode is conceived to be within the normal operating voltage range, hence possible with battery-powered devices, and with bursts at a frequency of a few to several times higher than the normal operating frequency which is around 350 kHz, hence at a frequency of for example 3 MHz and with a duration from under 1 second to several seconds. Applicant has discovered that this bubble eliminating piezo-actuation mode can be adapted to the liquid properties and to the dimensions of space 13, 131 and 132.

Hence the electronic means and piezo-electric actuator 40 complement and enhance the capability and reliability of the fluidic part, in particular the fluidic feed and outlet means of the volatile liquid droplet dispenser device to generate the right combination of droplet size and flow rates for a range of volatile liquids as well as by eliminating entrapped bubbles.

In summary, thanks to the decoupling of the liquid inlet means and the liquid outlet means on the horizontal plane for some liquids and preferred embodiments as well as on both the horizontal and the vertical plane for others, a controlled amount of liquid is allowed to enter the volatile liquid droplet dispenser device so that a reliable liquid feed is assured and hence a controlled release of droplets is possible.

Further, this decoupling, resulting in an eccentric arrangement of the liquid inlet and outlet means, even whilst being substantially in the same plane, or with the outlet means in a lower plane, allows for the use of a more effective piezoelectric vibrating element which results in a device that can be easily controlled in a precise manner.

These results are further improved through the other described preferred embodiments, allowing extension to further liquids and liquid properties and delivery conditions and through the actuation modes of piezo-electric actuator 40 which increase the flexibility and most of all the reliability of the micro-fluidics through the inventive entrapped bubble elimination electronic signal processing.

As mentioned above, the present volatile liquid droplet dispenser device may be used for several applications including respiratory therapy or aromatherapy. Further, it may of course be incorporated into an apparatus or electrical appliance. For example, such apparatus may be a vacuum-cleaner, a floor cleaner, robotics to clean a room, an aromatherapy apparatus, a respiratory therapy apparatus, an air-freshener, a fragrancer, an air purifier, an air conditioner, an insecticide dispensing apparatus, an ironing machine, a white goods appliance or an individual communication apparatus.

Generally speaking, however, the invention broadly pertains to a volatile liquid droplet dispenser device for containing a liquid substance to be dispensed, wherein the dispenser device includes (a) a first substrate having a space for containing the liquid substance, and having liquid outlet means comprising at least one outlet nozzle, and the first substrate further has the space arranged proximate to the liquid outlet means and to receive the liquid substance such that the liquid substance may exit the space of the device by traversing the at least one nozzle of the outlet means, (b) a second substrate having a liquid inlet means, and (c) an actuating membrane arranged to actuate liquid substance in the space. According to the invention, the first substrate further comprises a fluidic channel interconnected to the space and arranged to laterally connect the liquid inlet means to the space thereby conveying the liquid substance to the space by way of lateral capillary action, and the outlet means is arranged eccentric to the liquid inlet means and in a vertical plane that is substantially the same or lower than the plane of the liquid inlet means depending on the liquid substance properties dimensions.

Having described now the preferred embodiments of this invention, it will be apparent to one of skill in the art that other embodiments incorporating its concept may be used. It is felt, therefore, that this invention should not be limited to the disclosed embodiment, but rather should be limited only by the scope of the appended claims.

The invention claimed is:

1. A volatile liquid droplet dispenser device for containing a liquid substance to be dispensed, wherein the volatile liquid droplet dispenser device comprises:
   (a) a first substrate having a space for containing a liquid substance, the first substrate having a liquid outlet formed therein, wherein the liquid outlet comprises at least one outlet nozzle arranged to eject liquid substance therethrough, wherein the space is in fluid connection with the liquid outlet, wherein during normal operation the liquid substance exits the space by traversing the at least one outlet nozzle of the liquid outlet, wherein the liquid outlet comprises a substrate having one or more perforated portions and one or more additional portions having a greater thickness than the perforated portions;
   (b) a second substrate having a liquid inlet disposed to allow liquid substance to enter the volatile liquid droplet dispenser device; and
   (c) an actuating membrane arranged to generate and transmit vibrations to directly actuate liquid substance in the space to cause a pressure increase within the liquid substance so that the liquid substance undergoes a vibration and in response contacts the liquid outlet and exits the volatile liquid droplet dispenser device as a liquid droplet spray, wherein the first substrate further comprises a fluidic channel interconnected to the space and arranged to laterally connect the liquid inlet to the space thereby conveying the liquid substance to the space by way of lateral capillary action; wherein the liquid outlet is arranged eccentric to the liquid inlet, wherein said first substrate has a recess in a first main surface, and wherein the recess constitutes a space arranged to contain the liquid substance, and wherein said fluidic channel contains a plurality of microchannels arranged in the first main surface of said first substrate.

2. A volatile liquid droplet dispenser device according to claim 1, further comprising:
   (d) a first reservoir disposed to contain liquid substance.

3. A volatile liquid droplet dispenser device according to claim 2, wherein said first reservoir is an external reservoir, and wherein said first substrate or said second substrate operatively connected to receive said external reservoir.

4. A volatile liquid droplet dispenser device according to claim 2, wherein said first reservoir is an internal reservoir integrated into the volatile liquid droplet dispenser device.

5. A volatile liquid droplet dispenser device according to claim 4, wherein said first substrate has a recess in the first main surface, wherein the recess constitutes a space arranged to contain the liquid substance, and wherein said space is arranged to contain said internal reservoir.

6. A volatile liquid droplet dispenser device for containing a liquid substance to be dispensed, wherein the volatile liquid droplet dispenser device comprises:
   (a) a first substrate having a space for containing a liquid substance, the first substrate having a liquid outlet formed therein, wherein the liquid outlet comprises at least one outlet nozzle arranged to eject liquid substance therethrough, wherein the space is in fluid connection with the liquid outlet, wherein during normal operation the liquid substance exits the space by traversing the at least one outlet nozzle of the liquid outlet, wherein the liquid outlet comprises a substrate having one or more perforated portions and one or more additional portions having a greater thickness than the perforated portions;
   (b) a second substrate having a liquid inlet disposed to allow liquid substance to enter the volatile liquid droplet dispenser device; and
   (c) an actuating membrane arranged to generate and transmit vibrations to directly actuate liquid substance in the space to cause a pressure increase within the liquid substance so that the liquid substance undergoes a vibration and in response contacts the liquid outlet and exits the volatile liquid droplet dispenser device as a liquid droplet spray, wherein the first substrate further comprises a fluidic channel interconnected to the space and arranged to laterally connect the liquid inlet to the space thereby conveying the liquid substance to the space by way of lateral capillary action; wherein the liquid outlet is arranged eccentric to the liquid inlet, wherein said first substrate has a recess in a first main surface, and wherein the recess constitutes a space arranged to contain the liquid substance, and wherein said first substrate further has a through hole traversing said recess and an other main surface of said first substrate, and wherein said liquid outlet is arranged in the through hole so as to delimit said recess in said first main surface thus closing the through hole.

7. A volatile liquid droplet dispenser device according to claim 1, wherein said actuating membrane is arranged in between the first substrate and the second substrate and delimits said space.

8. A volatile liquid droplet dispenser device according to claim 1, further comprising:
   (d) a programmable microcontroller that controls said actuating membrane by varying an operating frequency, and by varying a supply voltage, wherein the operating frequency range and the supply voltage are chosen to correspond to a range of viscosities and a particular droplet size.

9. A volatile liquid droplet dispenser device according to claim 1, wherein said fluidic channel comprises a wick.

10. A volatile liquid droplet dispenser device according to claim 1, wherein said fluidic channel is formed in a metal plate.

11. A volatile liquid droplet dispenser device according to claim 1, wherein said fluidic channel also comprises a buffer reservoir.

12. A volatile liquid droplet dispenser device according to claim 1, wherein said liquid inlet comprises a wick.

13. A volatile liquid droplet dispenser device according to claim 3, wherein said liquid inlet is a tube arranged to extend into the external reservoir.

14. A volatile liquid droplet dispenser device according to claim 1, wherein said actuating membrane is formed of a first part and a second part that are arranged in a slideable arrangement with respect to each other.

15. A volatile liquid droplet dispenser device according to claim 3, wherein said external reservoir comprises a collapsible bag linked to said liquid inlet.

16. A volatile liquid droplet dispenser device according to claim 1, further comprising:
   (d) a vent disposed to vent air bubbles contained in the liquid substance from the volatile liquid droplet dispenser device.

17. A volatile liquid droplet dispenser device according to claim 8, further comprising:
   (e) a vent, and
   wherein said programmable microcontroller is further arranged to actuate said actuating membrane in a bubble-eliminating mode for driving any air bubbles contained in the liquid substance towards the vent by applying bursts at a frequency of a few to several times higher than the normal operating frequency and with a duration from under 1 second to several seconds.

18. An apparatus comprising a volatile droplet dispenser device according to claim 1, wherein said apparatus is selected from the group consisting of a vacuum-cleaner, a floor cleaner, robotics to clean a room, an aromatherapy apparatus, a respiratory therapy apparatus, an air-freshener, a fragrancer, an air purifier, an air conditioner, an insecticide dispensing apparatus, an ironing machine, a white goods appliance and an individual communication apparatus.

* * * * *